United States Patent
Koo et al.

(10) Patent No.: US 11,781,071 B2
(45) Date of Patent: Oct. 10, 2023

(54) CROSS-LINKING AGENT COMPOUND, LIQUID CRYSTAL ALIGNMENT COMPOSITION COMPRISING THE SAME, METHOD OF PREPARING LIQUID CRYSTAL ALIGNMENT FILM, AND LIQUID CRYSTAL ALIGNMENT FILM AND LIQUID CRYSTAL DISPLAY USING THE SAME

(71) Applicant: LG CHEM, LTD., Seoul (KR)

(72) Inventors: Kichul Koo, Daejeon (KR); Seongku Kim, Daejeon (KR); Minju Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 593 days.

(21) Appl. No.: 17/043,956

(22) PCT Filed: Nov. 11, 2019

(86) PCT No.: PCT/KR2019/015279
§ 371 (c)(1),
(2) Date: Sep. 30, 2020

(87) PCT Pub. No.: WO2020/105927
PCT Pub. Date: May 28, 2020

(65) Prior Publication Data
US 2021/0122979 A1    Apr. 29, 2021

(30) Foreign Application Priority Data
Nov. 20, 2018   (KR) .................... 10-2018-0143861

(51) Int. Cl.
| | | |
|---|---|---|
| C09K 19/56 | (2006.01) | |
| C07D 413/06 | (2006.01) | |
| C07D 413/14 | (2006.01) | |
| C07F 7/18 | (2006.01) | |
| C09D 5/00 | (2006.01) | |
| C09D 179/08 | (2006.01) | |
| G02F 1/1337 | (2006.01) | |
| C07F 7/08 | (2006.01) | |

(52) U.S. Cl.
CPC ............ C09K 19/56 (2013.01); C07D 413/06 (2013.01); C07D 413/14 (2013.01); C07F 7/0816 (2013.01); C07F 7/1804 (2013.01); C09D 5/00 (2013.01); C09D 179/08 (2013.01); G02F 1/133711 (2013.01)

(58) Field of Classification Search
CPC ...... C07F 7/0816; C07F 7/1804; C09K 19/56; C07D 413/06; C07D 413/14
See application file for complete search history.

(56) References Cited

U.S. PATENT DOCUMENTS

| | | |
|---|---|---|
| 3,468,851 A | 9/1969 | Yoda et al. |
| 3,527,657 A | 9/1970 | Huther et al. |
| 6,090,909 A | 7/2000 | Kato et al. |
| 9,758,622 B2 | 9/2017 | Jeon et al. |
| 10,054,820 B2 | 8/2018 | Kang et al. |
| 2016/0009860 A1 | 1/2016 | Fevre et al. |
| 2018/0348578 A1 | 12/2018 | Jo et al. |
| 2020/0063035 A1 | 2/2020 | Kwon et al. |

FOREIGN PATENT DOCUMENTS

| | | |
|---|---|---|
| CN | 107434772 A | 12/2017 |
| FR | 1448897 A | 8/1966 |
| KR | 10-1998-0035624 A | 8/1998 |
| KR | 10-1999-0072544 A | 9/1999 |
| KR | 10-2013-0097725 A | 9/2013 |
| KR | 10-2013-0130033 A | 11/2013 |
| KR | 10-2016-0047030 A | 5/2016 |
| KR | 10-2016-0098585 A | 8/2016 |
| KR | 10-2017-0143365 A | 12/2017 |
| KR | 10-2018-0010337 A | 1/2018 |
| KR | 10-2019-0044278 A | 4/2019 |
| KR | 10-2019-0050670 A | 5/2019 |
| KR | 10-2019-0087819 A | 7/2019 |
| WO | 2012-177061 A2 | 12/2012 |
| WO | 2017-222281 A2 | 12/2017 |

OTHER PUBLICATIONS

International Search Report Issued for International Application No. PCT/KR2019/015279 dated Mar. 3, 2020, 4 pages.
Heludyakov, V. D. et. al., "Synthesis of Carbofunctional Organosilicon Compounds. New Silicon-Containing Heterocycles", Chemischer Informationsdienst, 1981, vol. 12, No. 28, Abstract 268.
Extended European Search Report dated Jan. 22, 2021, of the corresponding European Patent Application No. 19886270.8, 6 pages.

*Primary Examiner* — Vickey Nerangis
(74) *Attorney, Agent, or Firm* — ROTHWELL, FIGG, ERNST & MANBECK, P.C.

(57) ABSTRACT

The present invention relates to a cross-linking agent compound of which end functional group is substituted with a protection group of a specific structure, a liquid crystal alignment composition comprising the cross-linking agent compound and polymer containing repeat units of polyimide or a precursor thereof, a method of preparing liquid crystal alignment film, a liquid crystal alignment film, and a liquid crystal display using the same.

13 Claims, No Drawings

CROSS-LINKING AGENT COMPOUND, LIQUID CRYSTAL ALIGNMENT COMPOSITION COMPRISING THE SAME, METHOD OF PREPARING LIQUID CRYSTAL ALIGNMENT FILM, AND LIQUID CRYSTAL ALIGNMENT FILM AND LIQUID CRYSTAL DISPLAY USING THE SAME

CROSS-REFERENCE TO RELATED APPLICATION(S)

This application is a 35 U.S.C. 371 National Phase Entry Application from PCT/KR2019/015279 filed on Nov. 11, 2019, designating the United States, which claims the benefit of Korean Patent Application No. 10-2018-0143861 filed on Nov. 20, 2018 with the Korean Intellectual Property Office, the disclosures of which are herein incorporated by reference in their entirety.

TECHNICAL FIELD

The present invention relates to a cross-linking agent compound having excellent solubility and improved cross-linking effect, a liquid crystal alignment composition that may have improved dispersibility and thus high reliability, and can afford excellent film strength when synthesizing a liquid crystal alignment film, and simultaneously, can realize improved alignment property and electrical properties, a method for preparing a liquid crystal alignment film using the same, and a liquid crystal alignment film and a liquid crystal display using the same.

BACKGROUND OF THE INVENTION

In a liquid crystal display, a liquid crystal alignment film performs a function for aligning liquid crystals in a constant direction. Specifically, the liquid crystal alignment film functions as a director in the arrangement of liquid crystal molecules, and thus, when liquid crystals move by an electric field to form an image, it makes them headed in a proper direction. In order to obtain uniform brightness and high contrast ratio in a liquid crystal display, it is essential to uniformly align liquid crystals As one of the existing methods of aligning liquid crystals, a method of applying a polymer film such as polyimide on a substrate such as glass, and rubbing the surface to a constant direction using fiber such as nylone or polyester was used. However, such a rubbing method may generate powdery dust or electrical discharge (ESD) when the fiber and polymer film are rubbed, thus causing a serious problem when preparing a liquid crystal panel.

In order to solve the problem of the rubbing method, a photo-alignment method is being recently studied, wherein anisotropy is induced to a polymer film by light irradiation instead of friction, and liquid crystals are arranged using the anisotropy.

As the material that can be used in the photo-alignment method, various materials have been introduced, and among them, polyimide is being mainly used for good performances of a liquid crystal alignment film. However, since polyimide has low solubility in a solvent, it is difficult to directly apply for a preparation process comprising coating in a solution state to form an alignment film.

Thus, a precursor such as polyamic acid or polyamic acid ester having excellent solubility is coated, which is then heat treated at 200° C. to 230° C. to form polyimide, which is irradiated by light, thereby progressing alignment treatment.

However, in order to obtain sufficient liquid crystal alignment property by light irradiation to a polyimide film, a lot of energy is required, and thus, there is a difficulty in securing productivity. Moreover, additional heat treatment is required so as to secure alignment stability after light irradiation, and as friction of column space (CS) is generated due to large panel, haze is generated on the surface of a liquid crystal alignment film, and thus, white dots are caused, and the performance of a panel cannot be sufficiently realized.

And, for the high quality driving of a liquid crystal display, high voltage holding ratio (VHR) should be exhibited, but polyimide has a limitation. Particularly, with a recent increase in demand for low power display, it was found out that a liquid crystal alignment agent may have an influence on the electrical properties such as afterimage generated by direct current/alternating current voltage, and voltage holding ratio, as well as alignment property of liquid crystals. Thus, there is an increasing demand for the development of liquid crystal alignment material capable of simultaneously realizing excellent liquid crystal alignment property and electrical properties.

Thus, a method of adding various cross-linking agents to a liquid crystal alignment composition has been suggested so as to prepare a liquid crystal alignment film having high film strength required in the field of displays, but due to insufficient solubility of the cross-linking agent compound, stability and dispersibility of the cross-linking agent decrease, and the liquid crystal alignment composition may not have uniformity, and thus, reliability decreases. Moreover, due to the simple addition of the cross-linking agent compound, electrical properties at high temperature, low frequency decrease. Thus, there was a difficulty in the preparation of a liquid crystal alignment film that can be applied for a high performance/low power display.

Thus, there is a demand for the development of a cross-linking agent compound that can prepare an alignment film having sufficient film strength, can increase alignment property and electrical properties of the alignment film, and may have high dispersibility in the composition.

BRIEF SUMMARY OF THE INVENTION

The present invention provides a cross-linking agent compound having excellent solubility and improved cross-linking effect.

The present invention also provides a liquid crystal alignment composition that comprises the cross-linking agent compound and thus has improved dispersibility and high reliability, and may afford excellent film strength when synthesizing a liquid crystal alignment film, and simultaneously, may realize improved alignment property and electrical properties.

The present invention further provides a method for preparing a liquid crystal alignment film using the liquid crystal alignment composition.

The present invention also provides a liquid crystal alignment film comprising the aligned and cured product of the liquid crystal alignment composition, and a liquid crystal display comprising the same.

A cross-linking agent compound represented by the following Chemical Formula 1 is provided herein:

[Chemical Formula 1]

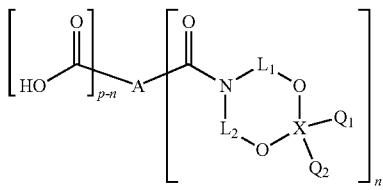

in the Chemical Formula 1,

A is a p-valent functional group, p is an integer of 1 to 4, n is an integer of 1 to 4, $L_1$ and $L_2$ are identical to or different from each other, and each independently, a C1-10 alkylene group, $Q_1$ and $Q_2$ are identical to or different from each other, and each independently, hydrogen, a C1-10 alkyl group, or a C6-20 aryl group, and X is a Group 14 element.

A liquid crystal alignment composition is also provided herein, which comprises the cross-linking agent compound represented by the Chemical Formula 1; and liquid crystal alignment polymer comprising one or more selected from the group consisting of a polyamic acid repeat units, a polyamic acid ester repeat units, and a polyimide repeat units.

A method for preparing a liquid crystal alignment film is also provided herein, which method comprises steps of: applying the liquid crystal alignment composition on a substrate to form a coating; drying the coating; irradiating light to the coating or rubbing the coating to progress alignment treatment; and heat treating the alignment-treated coating to cure.

A liquid crystal alignment film comprising the aligned and cured product of the liquid crystal alignment composition, and a liquid crystal display comprising the same are also provided herein.

Hereinafter, a cross-linking agent compound, a liquid crystal alignment composition comprising the same, a method for preparing a liquid crystal alignment film using the same, and a liquid crystal alignment film using the same, and a liquid crystal display comprising the same according to specific embodiments of the invention will be explained in more detail.

DETAILED DESCRIPTION OF THE INVENTION

Throughout the specification, the following terms may be defined as follows, unless specifically limited.

As used herein, when any part "comprises" any constructional element, it does not mean that other constructional elements are excluded, but it means that other constructional elements can be further included, unless described to the contrary.

As used herein, the term "substitution" means that another functional group bonds instead of a hydrogen atom in the compound, and the substituted position is not limited as long as it is a position where a hydrogen atom is substituted, namely, a substituent can be substituted, and in case substituted with two or more substituents, the two or more substituents may be identical to or different from each other.

As used herein, the term "unsubstituted or substituted" means unsubstituted or substituted with one or more substituents selected from the group consisting of deuterium; a halogen group; a cyano group; a nitro group; a hydroxyl group; a carbonyl group; an ester group; an imide group; an amide group; an amino group; a carboxy group; a sulfonic acid group; a sulfone amide group; a phosphine oxide group; an alkoxy group; an aryloxy group; an alkyl thioxy group; an aryl thioxy group; an alkyl sulfonyl group; an aryl sulfonyl group; a silyl group; a boron group; an alkyl group; a cycloalkyl group; an alkenyl group; an aryl group; an aralkyl group; an aralkenyl group; an alkylaryl group; an arylphosphine group; or a heterocyclic group containing one or more selected from N, O and S atoms, or unsubstituted or substituted with a substituent in which two or more of the above described substituents are connected. For example, "a substituent in which two or more substituents are connected" may be a biphenyl group. Namely, a biphenyl group may be an aryl group, or it may be interpreted as a substituent in which two phenyl groups are connected.

As used herein, ⟂ , or ——* means a bond connected to other substituents, and a direct bond means a case wherein any atom does not exist in a part indicated by L.

An alkyl group may be linear or branched, and the carbon number is not specifically limited, but preferably 1 to 10. According to one embodiment, the carbon number of the alkyl group is 1 to 6. Specific examples of the alkyl group may include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cycloheptylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl, and the like, but are not limited thereto.

A C1-10 fluoroalkyl group may the C1-10 alkyl group of which one or more hydrogen atoms are substituted with fluorine, and a C1-10 fluoroalkoxy group may be the C1-10 alkoxy group of which one or more hydrogen atoms are substituted with fluorine.

Halogen may be fluorine (F), chlorine (Cl), bromine (Br) or iodine (I).

A Group 14 element may be carbon (C), silicon (Si), germanium (Ge), tin (Sn), or lead (Pb).

A Group 15 element may be nitrogen (N), phosphorus (P), arsenic (As), antimony (Sb) or bismuth (Bi).

A nitrogen oxide is a compound in which a nitrogen atom and an oxygen atom bond, and a nitrogen oxide functional group means a functional group including nitrogen oxide in the functional group. As the nitrogen oxide functional group, for example, a nitro group (—$NO_2$), and the like may be used.

An aryl group is a monovalent functional group derived from arene, and is not specifically limited, but preferably, has a carbon number of 6 to 20, and it may be a monocyclic aryl group or a polycyclic aryl group. As the monocyclic aryl group, a phenyl group, a biphenyl group, a terphenyl group, and the like may be mentioned, but not limited thereto. As the polycyclic aryl group, a naphthyl group, an anthracenyl group, a phenanthryl group, a pyrenyl group, a perylenyl group, a chrysenyl group, a fluorenyl group, and the like may be mentioned, but not limited thereto. The aryl group may be unsubstituted or substituted.

An arylene group is a divalent functional group derived from arene, and the above explanations about an aryl group may be applied thereto, except that it is a divalent functional group.

A multivalent functional group is a residue in which plural hydrogen atoms bonded to any compound are removed, and for example, a divalent functional group, a trivalent functional group, a tetravalent functional group may be mentioned. For example, a tetravalent functional group derived from cyclobutane means a residue in which any 4 hydrogen atoms bonded to cyclobutane are removed.

A direct bond or a single bond means that any atom or atomic group does not exist in corresponding position, and thus, the position is connected by a bond-line. Specifically, it means a case wherein any atom does not exist in a part indicated by $R_a$, or $L_b$ (a and b are respectively, an integer of 1 to 20) in the Chemical Formulas.

Throughout the specification, weight average molecular weight means weight average molecular weight converted in terms of polystyrene, measured by GPC method. During the process of measuring weight average molecular weight converted in terms of polystyrene measured by GPC, commonly known analysis equipment and detectors such as refractive index detector, and analysis columns may be used, and commonly applied temperature condition, solvent, flow rate may be applied. For example, using Polymer Laboratories PLgel MIX-B 300 mm length column and Waters PL-GPC220 device, at the evaluation temperature of 160° C., using 1,2,4-trichlorobenzene as a solvent, and at a flow rate of 1 mL/min, a sample is prepared at the concentration of 10 mg/10 mL and then fed in the amount of 200 μL, and using a calibration curve formed using a polystyrene standard, Mw value may be calculated. As the polystyrene standard, 9 kinds having molecular weight of 2,000/10,000/30,000/70,000/200,000/700,000/2,000,000/4,000,000/10,000,000 were used.

The cross-linking agent compound according to the present invention is characterized in that the end of a cross-linkable functional group, i.e., hydroxyl group (—OH) is substituted with a specific functional group, and thus, the end of the cross-linkable functional group and a protection group bond to form a cyclic structure.

The present inventors confirmed through experiments that in case in the cross-linking agent compound according to the present invention, the end of a cross-linkable functional group, i.e., hydroxyl group (—OH) is substituted with a specific functional group, as shown in the Chemical Formula 1, the solubility of the cross-linking agent compound may increase, and the cross-linking agent compound may be uniformly dispersed in a composition to which the cross-linking agent compound is added, thereby exhibiting excellent cross-linking effect, and completed the present invention.

The present inventors also confirmed through experiments that in case the end of the cross-linkable functional group, i.e., hydroxyl group (—OH) is substituted with a divalent functional group containing a Group 14 element, due to the inclusion of the divalent functional group, the end of the cross-linkable functional group and a protection group bond to form a cyclic structure, and the elimination speed of such a cyclic structure may decrease, and thus, crosslink may be formed at higher temperature than applying a tetravalent functional group derivative, and completed the present invention.

In case the functional group introduced at the end of the cross-linkable functional group of the cross-linking agent compound is heat treated to a temperature above 150° C., it may be detached and removed, and the hydroxyl group may be recovered at the end of the cross-linkable functional group, thus progressing a smooth cross-linking reaction, and at a temperature less than 150° C., a cross-linking reaction by the cross-linkable functional group may be inhibited, thus minimizing decrease in the solubility in the composition due to the formation of unnecessary crosslink structure.

Particularly, the present inventors confirmed through experiments that in case the cross-linking agent compound represented by the Chemical Formula 1 is applied for a liquid crystal alignment composition, the cross-linking agent compound of the present invention having excellent solubility may be uniformly dispersed in the liquid crystal alignment composition, and thus, the properties of the prepared liquid crystal alignment film may become uniform, and the reliability may be improved, and completed the present invention.

As explained above, since the functional group introduced at the end of the cross-linkable functional group of the cross-linking agent compound is detached and removed when heat treated to a temperature above 150° C., in case the cross-linking agent compound is used for a liquid crystal alignment agent, in the liquid crystal alignment composition maintained at a temperature less than 150° C., the structure of the cross-linking agent compound represented by the Chemical Formula 1 is maintained, thus inhibiting a cross-linking reaction between polyimide or a precursor polymer thereof and the cross-linking agent compound represented by the Chemical Formula 1. And, when the temperature increases above 150° C. while passing through a drying process, exposure process, curing process, and the like for preparing a liquid crystal alignment film from the liquid crystal alignment composition, the divalent functional group containing a Group 14 element is substituted with a hydrogen atom in the cross-linking agent compound represented by the Chemical Formula 1, and a cross-linking reaction between polyimide or a precursor polymer thereof and a cross-linking agent compound represented by the Chemical Formula 3 described below may be progressed.

Thus, the dispersibility of the cross-linking agent compound according to one embodiment and polyimide or precursor polymer thereof may be sufficiently improved, and during the preparation process of a liquid crystal alignment film according to another embodiment described below, through the cross-linking reaction between the cross-linking agent compound and polyimide or precursor polymer thereof in the composition, the strength of the alignment film may be improved, and excellent alignment property and electrical properties may be realized in the finally prepared liquid crystal alignment cell.

1. Cross-Linking Agent Compound

The cross-linking agent compound according to the present invention may have a specific chemical structure represented by the above Chemical Formula 1. The physical/chemical properties of the cross-linking agent compound seem to be derived from the above explained specific structure of the Chemical Formula 1.

In the Chemical Formula 1, A may be a p-valent functional group, p may be an integer of 1 to 4, and n may be an integer of 1 to 4. And, in the Chemical Formula 1, p may be equal to or greater than n. A is a functional group positioned at the center of the cross-linking agent compound, and to the end functional groups included in A, functional groups indicated by "[ ]" in the Chemical Formula 1 may bond as many as p.

Namely, in the Chemical Formula 1, if p is 1, A is a monovalent functional group. And, if p is 2, A is a divalent functional group. And, if p is 3, A is a trivalent functional group. And, if p is 4, A is a tetravalent functional group.

Preferably, in the Chemical Formula 1, p may be 2, n may be 2, and A may be one of a C1-10 alkylene group or a C6-30 arylene group.

Alternatively, in the Chemical Formula 1, p may be 4, n may be 4, and A may be one of the tetravalent functional groups described in the following Chemical Formula 2.

[Chemical Formula 2]

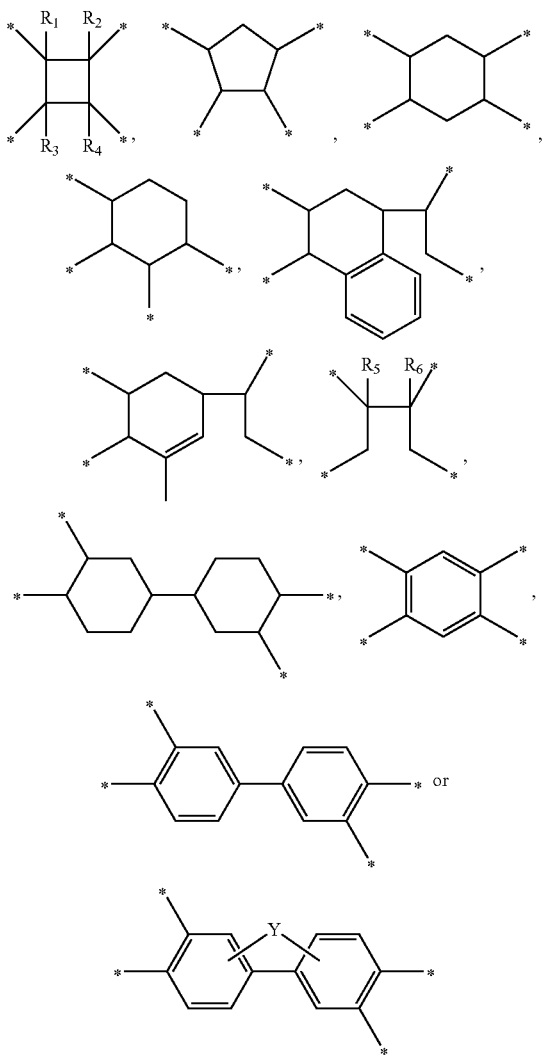

in the Chemical Formula 2, $R_1$ to $R_6$ are each independently, hydrogen, or a C1-10 alkyl group; Y is one selected from the group consisting of a direct bond, —O—, —CO—, —S—, —SO—, —SO$_2$—, —CR$_7$R$_8$—, —CONH—, —COO—, —(CH$_2$)$_b$—, —O(CH$_2$)$_b$O—, —COO—(CH$_2$)$_b$—OCO—, phenylene or a combination thereof; $R_7$ and $R_8$ are each independently, hydrogen, a C1-10 alkyl group, or a C1-10 haloalkyl group; and b is an integer of 1 to 10.

Alternatively, in the Chemical Formula 1, p may be 4, n may be 2, and A may be one of the tetravalent functional groups described in the above Chemical Formula 2.

In the Chemical Formula 1, $L_1$ and $L_2$ may be identical to or different from each other, and each independently, a C1-10 alkylene group, preferably a C1-5 alkylene group, for example, an ethylene group.

In the Chemical Formula 1, X, $Q_1$ and $Q_2$ are functional groups substituted for a hydrogen atom at the end of the cross-linkable functional group of the cross-linking agent compound, i.e., hydroxyl group (—OH), and they may inhibit the cross-linking reaction between polyimide or precursor polymer thereof and the cross-linking agent compound represented by the Chemical Formula 1.

As described below, the functional groups including X, $Q_1$ and $Q_2$ may be substituted with a hydrogen atom and detached when a temperature increases above 150° C., while passing through a drying process, an exposure process, and a curing process for preparing a liquid crystal alignment film from the liquid crystal alignment composition.

$Q_1$ and $Q_2$ may be identical to or different from each other, and each independently, hydrogen, a C1-10 alkyl group, or a C6-20 aryl group. Preferably, $Q_1$ and $Q_2$ may be each independently, a C1-10, or C1-5 alkyl group, for example, a methyl group.

In the Chemical Formula 1, X may be a Group 14 element. Specifically, X may be C or Si.

In the Chemical Formula 1, A may be a C1-10 alkylene group or a C6-30 arylene group, p may be 2, and n may be 2. Namely, the cross-linking agent compound represented by the Chemical Formula 1 may include a compound represented by the following Chemical Formula 1-1.

[Chemical Formula 1-1]

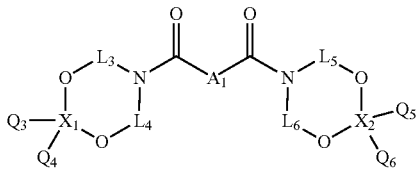

In the Chemical Formula 1-1, Ai is a divalent functional group; $L_3$ to $L_6$ are identical to or different from each other, and each independently, a C1-10 alkylene group; $Q_3$ to $Q_6$ are identical to or different from each other, and each independently, a C1-10 alkyl group or a C6-20 aryl group; and $X_1$ and $X_2$ are each independently, a Group 14 element.

More specifically, in the Chemical Formula 1-1, A1 is a C1-10 alkylene group or a C6-30 arylene group, $L_3$ to $L_6$ are identical to or different from each other, and each independently, a C1-5 alkylene group; $Q_3$ to $Q_6$ are identical to or different from each other, and each independently, a C1-5 alkyl group; and $X_1$ and $X_2$ are each independently, C or Si.

Representative examples of the compound represented by the Chemical Formula 1-1 are as follows.

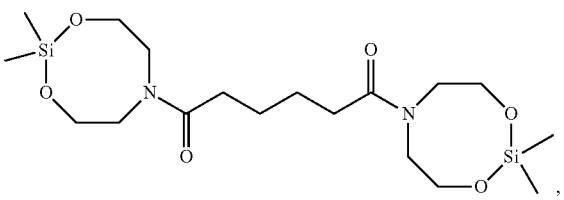

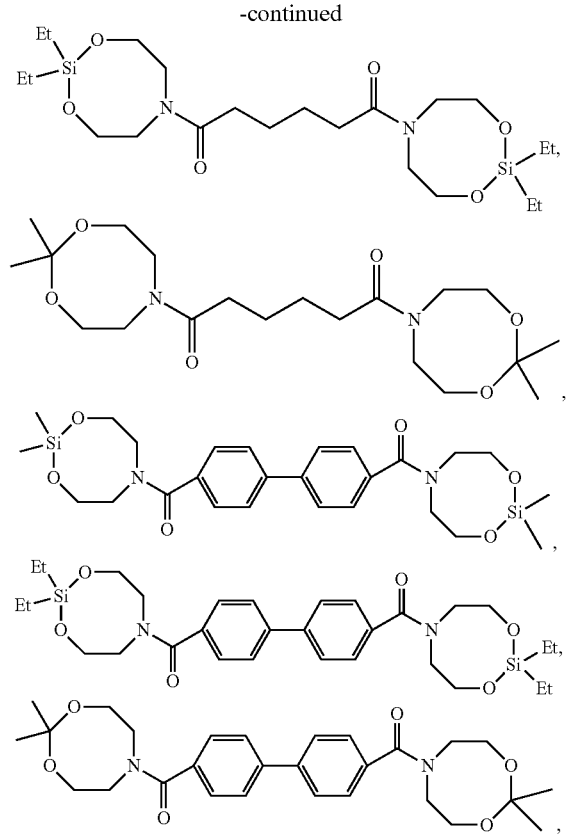

Alternatively, in the Chemical Formula 1, A may be a tetravalent functional group, p may be 4, and n may be 4. Namely, the cross-linking agent compound represented by the Chemical Formula 1 may include a compound represented by the following Chemical Formula 1-2.

[Chemical Formula 1-2]

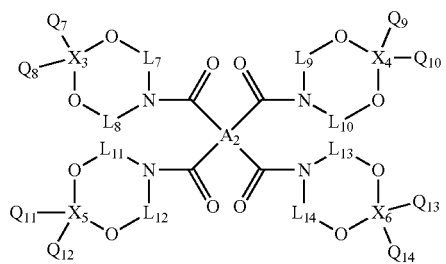

In the Chemical Formula 1-2, A2 is a tetravalent functional group; $L_7$ to $L_{14}$ are identical to or different from each other, and each independently, a C1-10 alkylene group; $Q_7$ to $Q_{14}$ are identical to or different from each other, and each independently, a C1-10 alkyl group or a C6-20 aryl group; and X3 to X6 are each independently, a Group 14 element.

More specifically, in the Chemical Formula 1-2, A2 is one of the tetravalent functional groups described in the Chemical Formula 2; $L_7$ to $L_{14}$ are identical to or different from each other, and each independently, a C1-5 alkylene group; $Q_7$ to $Q_{14}$ are identical to or different from each other, and each independently, a C1-5 alkyl group; and X3 to X6 are each independently, C or Si.

Representative examples of the compound represented by the Chemical Formula 1-2 are as follows.

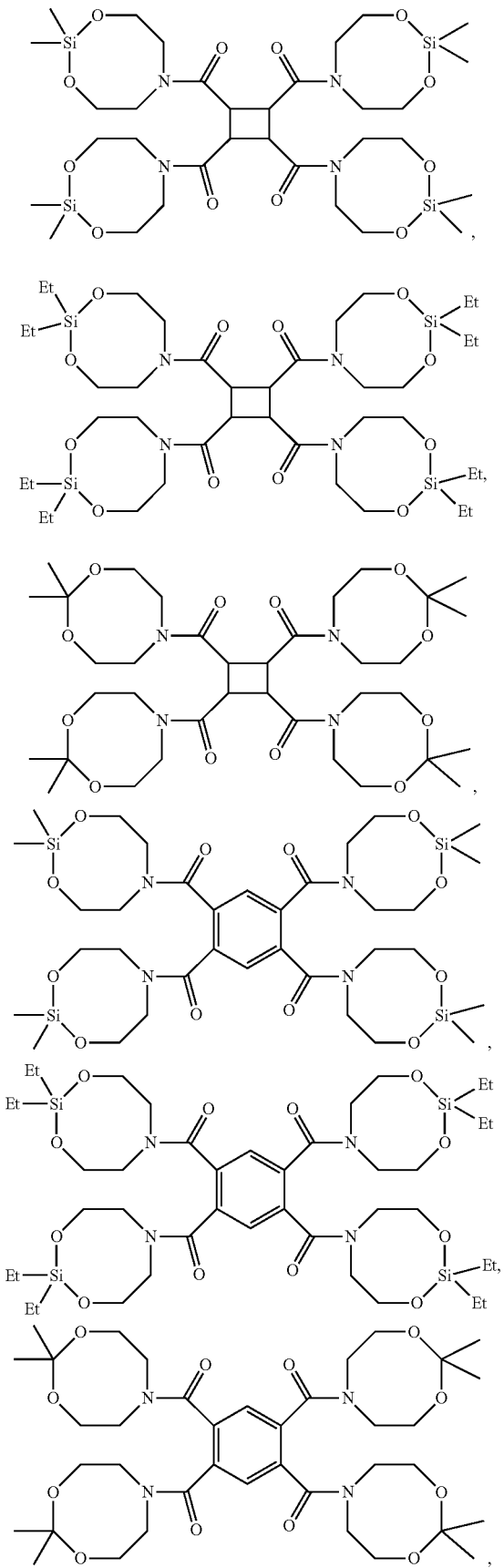

-continued

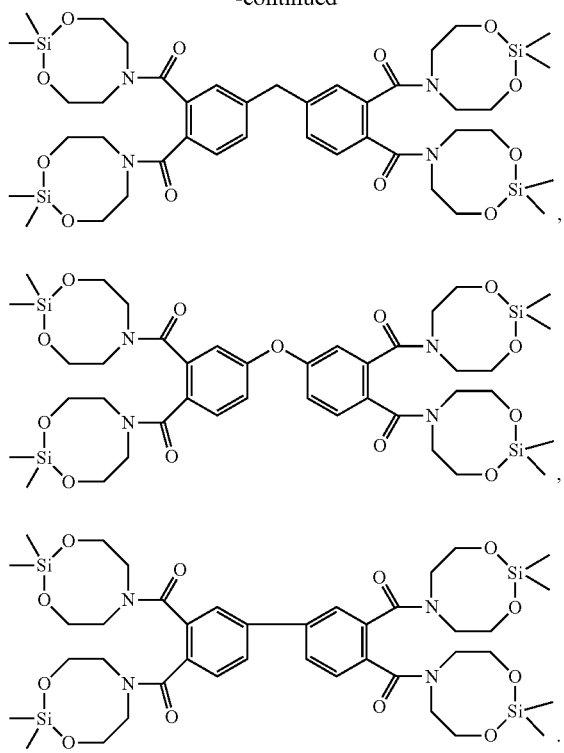

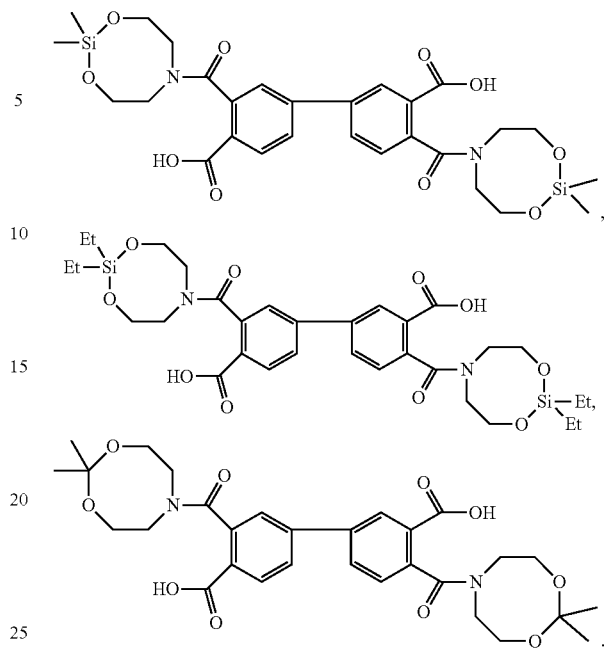

Alternatively, in the Chemical Formula 1, A may be a tetravalent functional group, p may be 4, and n may be 2. Namely, the cross-linking agent compound represented by the Chemical Formula 1 may include a compound represented by the following Chemical Formula 1-3.

[Chemical Formula 1-3]

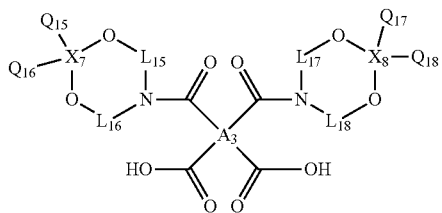

in the Chemical Formula 1-3, $A_3$ is a tetravalent functional group; L is to $L_{18}$ are identical to or different from each other, and each independently, a C1-10 alkylene group; $Q_{15}$ to $Q_{18}$ are identical to or different from each other, and each independently, a C1-10 alkyl group or a C6-20 aryl group, and $X_7$ to X8 are each independently, a Group 14 element.

More specifically, in the Chemical Formula 1-3, $A_3$ is one of the tetravalent functional groups described in the Chemical Formula 2; $L_{15}$ to $L_{18}$ are identical to or different from each other, and each independently, a C1-5 alkylene group; $Q_{15}$ to $Q_{18}$ are identical to or different from each other, and each independently, a C1-5 alkyl group, and $X_7$ to X8 are each independently, C or Si.

Representative examples of the compound represented by the Chemical Formula 1-3 are as follows.

Meanwhile, the cross-linking agent compound represented by the Chemical Formula 1 has excellent solubility in a solvent, and thus, if a solution in which the cross-linking agent compound is added to a solvent is observed with the unaided eye, it can be observed transparent.

In the Mathematical Formula 1, a mixed solution is a mixture of the cross-linking agent compound represented by the Chemical Formula 1 and a solvent. Examples of the solvent is not specifically limited, and as the solvent included in a liquid crystal alignment composition, for example, N,N-dimethylforamide, N,N-dimethylacetamide, N-methyl-2-pyrrolidone, N-methylcaprolactone, 2-pyrrolidone, N-ethylpyrrolidone, N-vinylpyrrolidone, dimethylsulfoxide, tetramethylurea, pyridine, dimethylsulfone, hexamethylsulfoxide, y-butyrolactone, 3-methoxy-N,N-dimethylpropaneamide, 3-ethoxy-N,N-dimethylpropaneamide, 3-buthoxy-N,N-dimethylpropaneamide, 1,3-dimethyl-imidazolidinone, ethylamylketone, methylnonylketone, methylethylketone, methylisoamylketone, methylisopropylketone, cyclohexanone, ethylene carbonate, propylene carbonate, diglyme, 4-hydroxy-4-methyl-2-pentanone, ethylene glycol monomethyl ether, ethylene glycol monomethyl ether acetate, ethylene glycol monoethyl ether, ethylene glycol monoethyl ether acetate, ethylene glycol monopropyl ether, ethylene glycol monopropyl ether acetate, ethylene glycol monoisopropyl ether, ethylene glycol monoisopropyl ether acetate, ethylene glycol monobutyl ether, ethylene glycol monobutyl ether acetate, and the like may be mentioned. These may be used alone or in combination.

In the mixed solution of the Mathematical Formula 1, the cross-linking agent compound represented by the Chemical Formula 1 may be included in the content of 1 wt % to 30 wt %, or 2 wt % to 25 wt %, or 10 wt % to 25 wt %, or greater than 10 wt % and 25 wt % or less, based on the total weight of the mixed solution.

Meanwhile, according to one embodiment of the invention, the cross-linking agent compound represented by the Chemical Formula 1 may be used for a liquid crystal alignment agent.

The cross-linking agent compound represented by the Chemical Formula 1, as explained above, has excellent solubility, and if heat treated to a temperature above 150° C., the functional groups introduced at the end are detached and removed, and the hydroxyl group is recovered at the end of the cross-linkable functional group, thus progressing a smooth cross-linking reaction, and such characteristics of the cross-linking agent compound of the present invention can be realized by the specific structure represented by the Chemical Formula 1.

Due to the above characteristics, in case the cross-linking agent compound represented by the Chemical Formula 1 is used for a liquid crystal alignment agent, the cross-linking agent compound may be uniformly dispersed in the liquid crystal alignment composition, and thus, the properties of the prepared alignment film may become uniform.

And, in the preparation process of a liquid crystal alignment film, at room temperature, cross-linkability is inhibited to sufficiently improve the dispersibility of the cross-linking agent compound and polyimide or precursor polymer thereof, and simultaneously, as a temperature increases above 150° C. while passing through a drying process, an exposure process, a curing process for preparing a liquid crystal alignment film, the hydroxyl group is recovered at the end of the cross-linkable functional group, and a cross-linking reaction with polyimide or precursor polymer thereof is progressed, thereby realizing a liquid crystal alignment film with improved film strength.

Since the cross-linking agent compound of the prior art has poor solubility, the stability and dispersibility of the cross-linking agent decreases, and thus, a liquid crystal alignment composition is not uniform, and the reliability decreases, or the electrical properties are lowered because a protection group is not included at the end. However, the cross-linking agent compound of the Chemical Formula 1 provided herein not only has excellent solubility, but also has excellent alignment property and electrical properties and affords sufficient film strength because the functional group introduced at the end protects the cross-linkable hydroxyl group.

2. Liquid Crystal Alignment Composition

Meanwhile, according to one embodiment of the invention, a liquid crystal alignment composition is provided, which comprises the cross-linking agent compound represented by the Chemical Formula 1; and liquid crystal alignment polymer comprising one or more selected from the group consisting of a polyamic acid repeat units, a polyamic acid ester repeat units, and a polyimide repeat units.

The cross-linking agent compound represented by the Chemical Formula 1 may be included in the content of 1 wt % to 30 wt %, or 2 wt % to 25 wt %, or 10 wt % to 25 wt %, or greater than 10 wt % and 25 wt % or less, based on the total weight of the liquid crystal alignment composition.

If the content of the cross-linking agent compound excessively increases, the cross-linking degree of the liquid crystal alignment polymer may excessively increases, and thus, the flexibility of the polymer may decrease, and due to increase in the viscosity of the composition, storage stability may decrease and dispersibility of the cross-linking agent in the composition may decrease, or due to gelation in the composition, coatability on a substrate may decrease.

To the contrary, if the content of the cross-linking agent compound excessively decreases, it may be difficult to sufficiently realize the effect for improving mechanical strength and electrical properties by increasing the cross-linking degree of the liquid crystal alignment polymer.

Meanwhile, the liquid crystal alignment composition may comprise liquid crystal alignment polymer comprising first liquid crystal alignment polymer comprising one or more kinds of repeat units selected from the group consisting of repeat units represented by the following Chemical Formula 4, repeat units represented by the following Chemical Formula 5, and repeat units represented by the following Chemical Formula 6; and second liquid crystal alignment polymer comprising one or more kinds of repeat units selected from the group consisting of repeat units represented by the following Chemical Formula 7, repeat units represented by the following Chemical Formula 8, and repeat units represented by the following Chemical Formula 9:

[Chemical Formula 4]

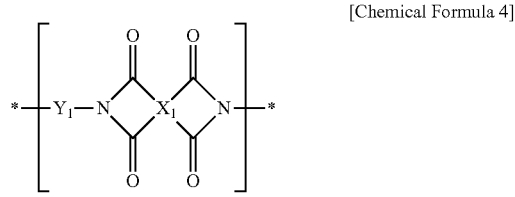

[Chemical Formula 5]

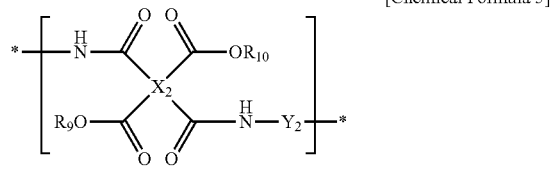

[Chemical Formula 6]

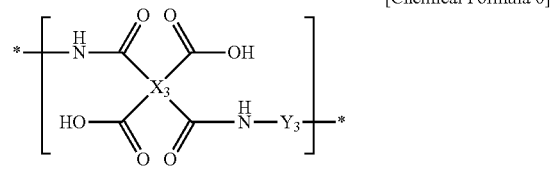

[Chemical Formula 7]

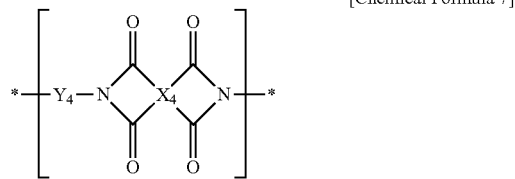

[Chemical Formula 8]

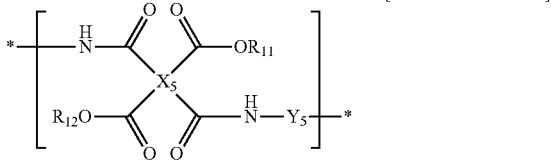

[Chemical Formula 9]

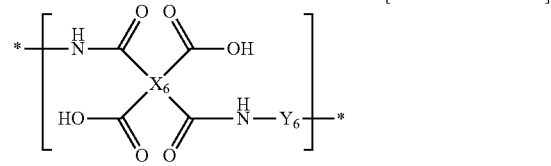

in the Chemical Formulas 4 to 9, at least one of $R_9$ and $R_{10}$ is a C1-10 alkyl group, and the other is hydrogen, at least one of $R_{11}$ and $R_{12}$ is a C1-10 alkyl group, and the other is hydrogen, $X_1$ to $X_6$ are each independently, a tetravalent organic group represented by the following Chemical Formula 10,

[Chemical Formula 10]

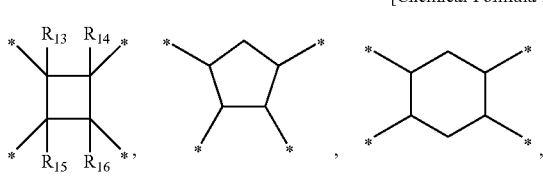
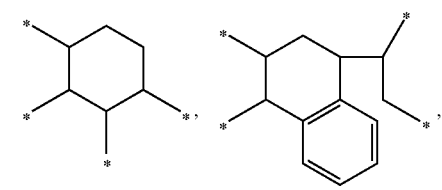
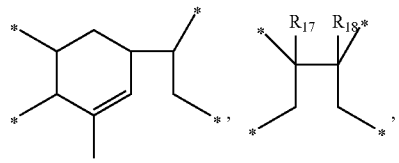
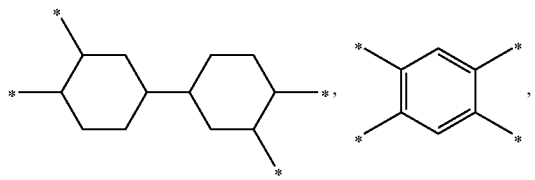
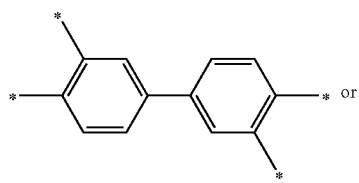
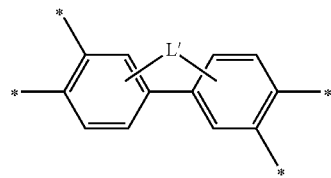

in the Chemical Formula 10, $R_{13}$ to $R_{18}$ are each independently, hydrogen, or a C1-6 alkyl group, L' is one selected from the group consisting of a single bond, —O—, —CO—, —COO—, —S—, —SO—, —SO$_2$—, —CR$_{19}$R$_{20}$—, —(CH$_2$)$_z$—, —O(CH$_2$)$_z$O—, —COO(CH$_2$)$_z$OCO—, —CONH—, or phenylene, wherein $R_{19}$ and $R_{20}$ are each independently, hydrogen, a C1-10 alkyl group, or a C1-10 haloakyl group, and z is an integer of 1 to 10, $Y_1$ to $Y_3$ are each independently, a divalent organic group represented by the following Chemical Formula 11,

[Chemical Formula 11]

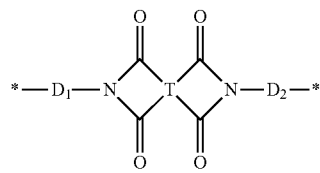

in the Chemical Formula 11,

T is the tetravalent organic group represented by the Chemical Formula 10, $D_1$ and $D_2$ are each independently, a C1-20 alkylene group, a C1-10 heteroalkylene group, a C3-20 cycloalkylene group, a C6-20 arylene group, or a C2-20 heteroarylene group, $Y_4$ to $Y_6$ are each independently, a divalent organic group represented by the following Chemical Formula 12,

[Chemical Formula 12]

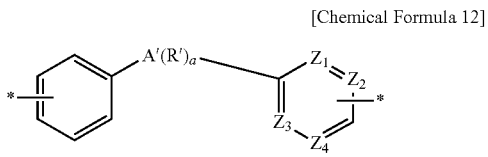

in the Chemical Formula 12,

A' is a Group 15 element,

R' is hydrogen, or a C1-10 alkyl group, a is an integer of 1 to 3, and at least one of $Z_1$ to $Z_4$ is nitrogen, and the others are carbon.

Specifically, the first liquid crystal alignment polymer may comprise one kind of the repeat units represented by the following Chemical Formula 4, the repeat units represented by the following Chemical Formula 5, and the repeat units represented by the following Chemical Formula 6, or a mixture of two kinds thereof, or a mixture of all the three kinds thereof.

And, the second liquid crystal alignment polymer may comprise one kind of the repeat units represented by the following Chemical Formula 7, the repeat units represented by the following Chemical Formula 8, and the repeat units represented by the following Chemical Formula 9, or a mixture of two kinds thereof, or a mixture of all the three kinds thereof.

Specifically, in the first liquid crystal alignment polymer, and the second liquid crystal alignment polymer of the liquid crystal alignment composition according to one embodiment, $X_1$ to $X_6$ may be each independently, a tetravalent organic group represented by the Chemical Formula 10. The $X_1$ to $X_6$ may be functional groups derived from tetracarboxylic acid anhydride used for the synthesis of polyamic acid, polyamic acid ester, or polyimide.

In the Chemical Formula 10, $R_{13}$ to $R_{18}$ are each independently, hydrogen, or a C1-6 alkyl group; L' is one selected from the group consisting of a single bond, —O—, —CO—, —COO—, —S—, —SO—, —SO$_2$—, —CR$_{19}$R$_{20}$—, —(CH$_2$)$_z$—, —O(CH$_2$)$_z$O—, —COO(CH$_2$)$_z$OCO—, —CONH—, or phenylene, wherein $R_{19}$ and $R_{20}$ are each independently, hydrogen, a C1-10 alkyl group, or a C1-10 haloakyl group, and z is an integer of 1 to 10, More specifically, the $X_1$ to $X_6$ may be each independently, an organic group of the following Chemical Formula 10-1 derived from 1,2,3,4-tetracarboxylic dianhydride, an organic group of the following Chemical Formula 10-2 derived from 1,3-dimethylcyclobutane-1,2,3,4-tetracarboxylic dianhydride, an organic group of the following Chemical Formula 10-3 derived from tetrahydro-[3,3'-bifurane]-2,2',5,5'-tetraone, an organic group of the following Chemical Formula 10-4 derived from 1,2,4,5-cyclohexane tetracarboxylic dianhydride, an organic group of the following Chemical Formula 10-5 derived from pyromellitic dianhydride, or an organic group of the following Chemical Formula 10-6 derived from 3,3',4,4'-biphenyltetracarboxylic dianhydride.

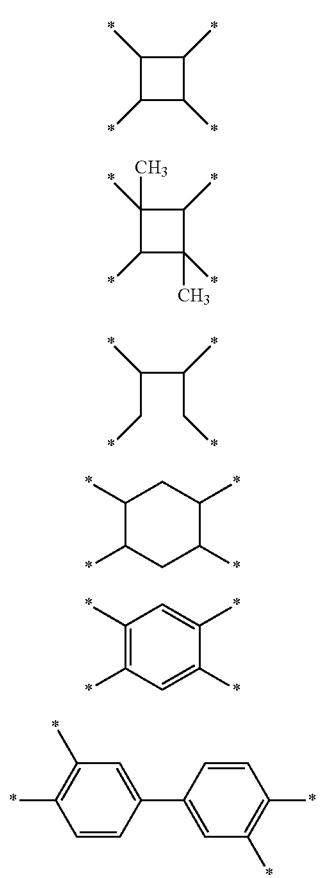

[Chemical Formula 10-1]

[Chemical Formula 10-2]

[Chemical Formula 10-3]

[Chemical Formula 10-4]

[Chemical Formula 10-5]

[Chemical Formula 10-6]

Meanwhile, the first liquid crystal alignment polymer of the liquid crystal alignment composition according to one embodiment may comprise repeat units of the Chemical Formulas 4 to 6 wherein $Y_1$ to $Y_3$ are each independently, a divalent organic group represented by the Chemical Formula 11. Since the first liquid crystal alignment polymer is synthesized from diamine containing imide repeat units already imidized, after forming a coating, light may be directly irradiated without high temperature heat treatment to induce anisotropy, and thereafter, heat treatment may be progressed to complete an alignment film, and thus, light irradiation energy may be significantly reduced, and a liquid crystal alignment film that not only has excellent alignment property and stability but also has excellent voltage holding ratio and electrical properties may be prepared even by a simple process comprising one heat treatment process.

Specifically, in the Chemical Formula 11, T may be a functional group represented by the following Chemical Formula 10-1 or a functional group represented by the following Chemical Formula 10-2.

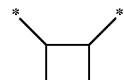

[Chemical Formula 10-1]

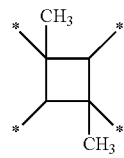

[Chemical Formula 10-2]

More specifically, although the examples of the organic groups represented by the Chemical Formula 11 are not specifically limited, for example, it may be a functional group represented by the following Chemical Formula 11-1 or Chemical Formula 11-2.

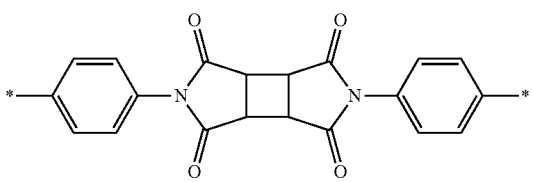

[Chemical Formula 11-1]

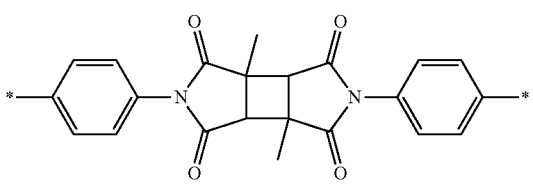

[Chemical Formula 11-2]

In the first liquid crystal alignment polymer, among the repeat units represented by the Chemical Formula 4, Chemical Formula 5 and Chemical Formula 6, the repeat units represented by the Chemical Formula 4 may be included in the content of 5 mol % to 74 mol %, or 10 mol % to 60 mol %, based on the total repeat units.

As explained above, if polymer comprising a certain amount of imide repeat units represented by the Chemical Formula 4 is used, the first liquid crystal alignment polymer comprises a certain amount of imide repeat units already imidized, and thus, even if light is directly irradiated without high temperature heat treatment, a liquid crystal alignment film having excellent alignment property and stability may be prepared.

If the content of the repeat units represented by the Chemical Formula 4 is less than the above range, sufficient alignment property may not be exhibited, and alignment stability may be lowered, and if the content of the repeat units represented by the Chemical Formula 4 is greater than the above range, it may be difficult to prepare a stable alignment solution that can be coated. Thus, it is preferable that the repeat units represented by the Chemical Formula 4 are included in the above range, so as to provide liquid crystal alignment polymer having excellent storage stability, electrical properties, alignment property and alignment stability.

And, the repeat units represented by the Chemical Formula 5 or the repeat units represented by the Chemical Formula 6 may be included in an appropriate content according to the aimed properties.

Specifically, the repeat units represented by the Chemical Formula 5 may be included in the content of 1 mol % to 60 mol %, preferably 5 mol % to 50 mol %, based on the total repeat units represented by the Chemical Formulas 4 to 6. Since the repeat units represented by the Chemical Formula 5 has low imide conversion rate during high temperature heat treatment after light irradiation, if the content is not fall within the above range, the region where it interacts with liquid may decrease, and thus, alignment property may be relatively deteriorated. Thus, the repeat units represented by the Chemical Formula 5 within the above range may provide liquid crystal alignment polymer that has excellent process property and can realize high imidization degree.

And, the repeat units represented by the Chemical Formula 6 may be included in the content of 0 mol % to 95 mol %, preferably 10 mol % to 80 mol %, based on the total repeat units represented by the Chemical Formulas 4 to 6. Within such range, excellent cotability may be exhibited, thus providing liquid crystal alignment polymer that has excellent process property and can realize high imidization degree.

Meanwhile, the second liquid crystal alignment polymer of the liquid crystal alignment composition according to one embodiment may comprise the repeat units of the Chemical Formulas 7 to 9 wherein $Y_4$ to $Y_6$ are each independently a divalent organic group represented by the Chemical Formula 12. $Y_4$, $Y_5$, $Y_6$ may be defined as a divalent organic group represented by the Chemical Formula 12 to provide liquid crystal alignment polymer of various structures that can exhibit the above explained effects.

As explained, since the second liquid crystal alignment polymer is synthesized from diamine containing specific organic functional groups represented by the Chemical Formula 12, high voltage holding ratio may be exhibited even under high temperature environment, and contrast ratio decrease or afterimage may be improved, thereby improving electrical properties.

In the Chemical Formula 12, A' may be a Group 15 element, which may be nitrogen (N), phosphorus (P), arsenic (As), tin (Sn) or bismuth (Bi). The R' is a functional group bonding to the A', and it may bond to A' element as many as the number represented by a. Preferably, in the Chemical Formula 12, A' is nitrogen, R' is hydrogen, and a is 1.

Meanwhile, in the Chemical Formula 12, since at least one of $Z_1$ to $Z_4$ is nitrogen and the others are carbon, the Chemical Formula 12 may form an asymmetric structure by the nitrogen atom wherein symmetry is not made based on the center point or center line. The Chemical Formula 12 is repeat units derived from diamine having a specific structure containing nitrogen atom and the like, which is a precursor used for the formation of liquid crystal alignment polymer, and asymmetric diamine described below is used.

The organic group represented by the Chemical Formula 12 has a structural characteristic in that two aromatic cyclic compounds, preferably a hetero aromatic cyclic compound and a aromatic cyclic compound bond by a secondary amine group or a tertiary amine group. Thus, while fulfilling the alignment property or afterimage property of a liquid crystal alignment agent more than equivalent level, voltage holding ratio may be improved to realize excellent electrical properties.

To the contrary, in case two aromatic cyclic compounds bond by a single bond without a secondary amine group or a tertiary amine group, the alignment property of a liquid crystal alignment agent may be poor, and the voltage holding ratio may remarkably decrease.

And, in case each of two aromatic cyclic compounds bonding through a secondary amine group or a tertiary amine group does not include a nitrogen atom, even if an imidization reaction with polyamic acid or polyamic acid ester that is formed by the reaction of amine and acid anhydride is progressed (for example, through 230° C. heat treatment), sufficient imidization reaction may not be progressed, and thus, an imidization degree may decrease in the final liquid crystal alignment film.

And, the organic group represented by the Chemical Formula 12 is characterized in that only an amine group and hydrogen bond to a hetero aromatic cyclic compound and an aromatic cyclic compound, respectively, and other substituents are not introduced. And, in case a substituent, for example, a fluoroalkyl group is introduced in the hetero aromatic cyclic compound or aromatic cyclic compound, the alignment property of a liquid crystal alignment agent may be poor, and a voltage holding ratio may remarkably decrease.

More specifically, in the Chemical Formula 12, one of $Z_1$ to $Z_4$ may be nitrogen, and others may be carbon, or in the Chemical Formula 12, one of $Z_1$ and $Z_3$ may be nitrogen, others may be carbon, and $Z_2$ and $Z_4$ may be carbon. Namely, in the Chemical Formula 12, the aromatic ring containing $Z_1$ to $Z_4$ may have a pyridine structure. Thus, a liquid crystal display device applying the liquid crystal alignment polymer of one embodiment may realize high voltage holding ratio and liquid crystal alignment property.

And, the Chemical Formula 12 may include one or more functional groups selected from the group consisting of the following Chemical Formula 12-1, Chemical Formula 12-2 and Chemical Formula 12-3.

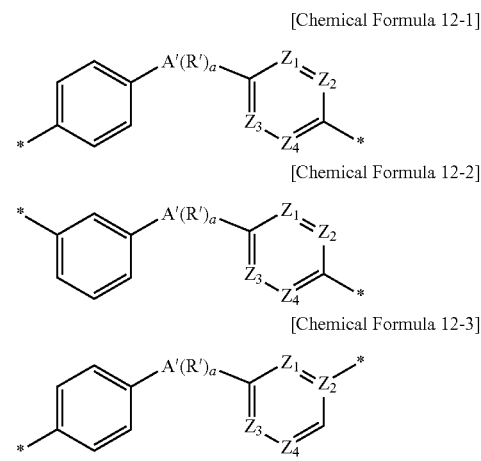

In the Chemical Formulas 12-1 to 12-3, A', $Z_1$ to $Z_4$, R', and a are as explained in the Chemical Formula 12.

As explained, when the organic group represented by the Chemical Formula 12 includes one or more functional groups selected from the group consisting of Chemical Formula 12-1, Chemical Formula 12-2, and Chemical Formula 12-3, more excellent liquid crystal alignment property may be realized.

More specifically, although the examples of the organic groups represented by the Chemical Formula 12 are not significantly limited, for example, one or more functional groups selected from the group consisting of the following Chemical Formula 12-4, Chemical Formula 12-5 and Chemical Formula 12-6 may be mentioned.

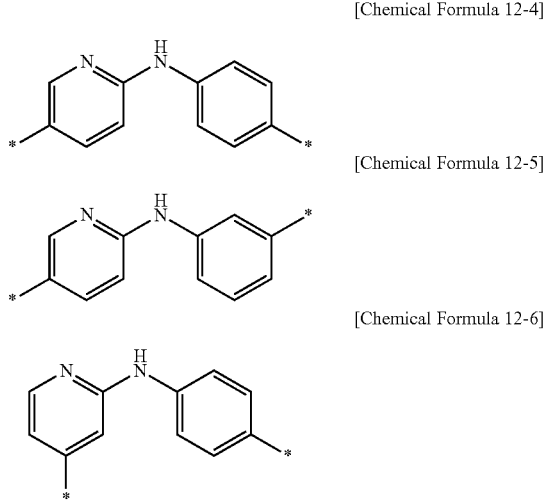

[Chemical Formula 12-4]

[Chemical Formula 12-5]

[Chemical Formula 12-6]

Meanwhile, the liquid crystal alignment composition according to one embodiment may comprise 10 to 1000 parts by weight, or 15 to 800 parts by weight of the second liquid crystal alignment polymer, based on 100 parts by weight of the first liquid crystal alignment polymer.

If the first liquid crystal alignment polymer and the second liquid crystal alignment polymer are mixed in the above weight ratio range, excellent photoreaction property and liquid crystal alignment property of the first liquid crystal alignment polymer and excellent electrical properties of the second liquid crystal alignment polymer may be complemented with each other, and thus, excellent coatability may be exhibited thus realizing excellent process property and high imidization degree, and a liquid crystal alignment film that has excellent electrical properties such as afterimage generated by direct current/alternating current voltage, voltage holding ratio, and the like, and has excellent alignment property and electrical properties may be prepared.

Although the weight average molecular weight (measured by GPC) of the first liquid crystal alignment polymer and the second liquid crystal alignment polymer is not significantly limited, for example, it may be 10000 g/mol to 200000 g/mol.

3. A Method for Preparing a Liquid Crystal Alignment Film

According to another embodiment of the invention, a method for preparing a liquid crystal alignment film using the liquid crystal alignment composition is provided. The method for preparing a liquid crystal alignment film comprises steps of: applying the liquid crystal alignment composition on a substrate to form a coating (step 1); drying the coating (step 2); irradiating light to the coating or rubbing the coating to progress alignment treatment (step 3); and heat treating the alignment-treated coating to cure (step 4).

In the step 1, the above explained liquid crystal alignment composition is applied on a substrate to form a coating. The details of the liquid crystal alignment composition include all the contents described in the above embodiment.

A method of applying the liquid crystal alignment composition on a substrate is not specifically limited, and for example, screen printing, offset printing, flexo printing, ink jet, and the like may be used.

And, the liquid crystal alignment composition may be dissolved or dispersed in an organic solvent. Specific examples of the organic solvent may include N,N-dimethylformamide, N,N-dimethylacetamide, N-methyl-2-pyrrolidone, N-methylcaprolactone, 2-pyrrolidone, N-ethylpyrrolidone, N-vinylpyrrolidone, dimethylsulfoxide, tetratmethylurea, pyridine, dimethylsulfone, hexamethylsulfoxide, γ-butyrolactone, 3-methoxy-N,N-dimethylpropaneamide, 3-ethoxy-N,N-dimethylpropaneamide, 3-buthoxy-N,N-dimethylpropaneamide, 1,3-dimethyl-imidazolidinone, ethylamylketone, methylnonylketone, methylethylketone, methylisoamylketone, methylisopropylketone, cyclohexanone, ethylenecarbonate, propylenecarbonate, diglyme, 4-hydroxy-4-methyl-2-pentanone, ethylene glycol monomethyl ether, ethylene glycol monomethyl ether acetate, ethylene glycol monoethyl ether, ethylene glycol monoethyl ether acetate, ethylene glycol monopropyl ether, ethylene glycol monopropyl ether acetate, ethylene glycol monoisopropyl ether, ethylene glycol monoisopropyl ether acetate, ethylene glycol monobutyl ether, ethylene glycol monobutyl ether acetate, and the like. These may be used alone or in combinations.

And, the liquid crystal alignment composition may further comprise other components, in addition to the organic solvent. As non-limiting examples, additives that can improve the uniformity of a film thickness or surface smoothness, improve adhesion of a liquid crystal alignment film and a substrate, change dielectric constant or conductivity of a liquid crystal alignment film, or increase denseness of a liquid crystal alignment film when the liquid crystal alignment composition is applied, may be additionally included. As such additives, various solvents, surfactants, silane-based compounds, dielectric substances or cross-linkable compounds, and the like may be mentioned.

In the step 2, the coating formed by applying the liquid crystal alignment composition on a substrate is dried.

The step of drying the coating may be conducted by heating, vacuum evaporation of the coating, and the like, and it may be preferably conducted at 50° C. to 150° C., or 60° C. to 140° C.

Meanwhile, in the step of applying the liquid crystal alignment composition on a substrate to form a coating, the pH of the liquid crystal alignment composition may be 4.0 to 6.0. Specifically, since reactivity of elimination of acetal or silyl ether increases under weakly acidic condition, the liquid crystal alignment composition may be weakly acidic, preferably have pH of 4.0 to 6.0.

In the step 3, light is irradiated to the coating to progress alignment treatment.

In the alignment treatment step, the coating may be a coating immediately after the drying step, or it may be a coating passing through heat treatment after the drying step. The "coating immediately after the drying step" means that light is immediately irradiated without progressing heat treatment to a temperature above the drying step, after the drying step, and other steps except heat treatment may be added.

More specifically, the existing method for preparing a liquid crystal alignment film using a liquid crystal alignment agent containing polyamic acid or polyamic acid ester essentially comprises a step of progressing high temperature heat treatment before light irradiation for the imidization of polyamic acid, while according to the method for preparing a liquid crystal alignment film using a liquid crystal alignment agent of the above embodiment, the heat treatment step is not included, and light is immediately irradiated to progress alignment treatment, and then, the alignment-treated coating is heat treated and cured, thereby preparing a alignment film.

And, in the step of alignment treatment, light irradiation may be conducted by irradiating polarized UV rays of 150 nm to 450 nm wavelength, Wherein, the intensity of light exposure may vary according to the kind of liquid crystal alignment polymer, and energy may be irradiated at 10 mJ/cm$^2$ to 10 J/cm$^2$, preferably 30 mJ/cm$^2$ to 2 J/cm$^2$.

Wherein, UV rays polarized by passing through or reflecting on a polarization device in which dielectric anisotropic material is coated on the surface of a transparent substrate such as quartz glass, soda lime glass, soda lime free glass, and the like, a polarization plate on which aluminum or metal wire is finely deposited, or a Brewster polarization device by reflection of quartz glass, and the like may be irradiated to progress alignment treatment. The polarized UV rays may be irradiated vertically to the surface of the substrate, or it may be irradiated while the incident angle is inclined at a specific angle. In this way, the alignability of liquid crystal molecules is imparted to the coating.

And, in the step of alignment treatment, rubbing may be conducted using rubbing cloth. More specifically, the rubbing treatment may be conducted by rubbing the surface of the heat-treated coating in one direction while rotating a rubbing roller having rubbing cloth attached to a metal roller In the step 4, the alignment-treated coating is heat treated to cure.

In the step of heat treating and curing the alignment-treated coating, the functional groups of the cross-linking agent compound represented by the Chemical Formula 1 in the alignment-treated coating may be substituted with hydrogen atoms and detached, and a cross-linking reaction between liquid crystal alignment polymers may be progressed.

Specifically, in the step of heat treating and curing the alignment-treated coating, a cross-linking agent compound represented by the following Chemical Formula 3 may be included in the alignment-treated coating.

[Chemical Formula 3]

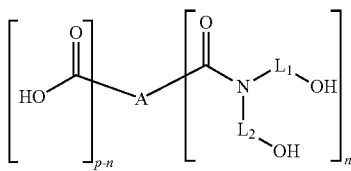

In the Chemical Formula 3, A, p, n, L$_1$, and L$_2$ are as defined in the Chemical Formula 1 of one embodiment. And, in the Chemical Formula 3, p may be equal to or greater than n.

In case the cross-linking agent compound represented by the Chemical Formula 3 is included in a liquid crystal alignment composition, cross-linking reactions may be progressed in the composition, and thus, it may be difficult for the cross-linking agent compound to be uniformly dispersed in the composition, and storage stability may also decrease.

To the contrary, in the liquid crystal alignment composition of the present invention, a cross-linking agent compound represented by the Chemical Formula 1 is added to inhibit a cross-linking reaction in the composition, and then, in the step of heat treating and curing the alignment-treated coating, the cross-linking agent compound represented by the Chemical Formula 1 may be spontaneously converted into the cross-linking agent compound represented by the Chemical Formula 3. Thus, the dispersibility and stability of the cross-linking agent compound in the composition may be increased, and the improvement effect of film strength may be realized through the formation of cross-link structures in an alignment film.

The step of heat treating and curing the alignment-treated coating is also conducted after light irradiation in the existing method of preparing a liquid crystal alignment film using liquid crystal alignment polymer containing polyamic acid or polyamic acid ester, and it is distinguished from the heat treatment step conducted before light irradiation, or conducted for the imidization of a liquid crystal alignment agent while irradiating light, after applying a liquid crystal alignment agent on a substrate.

Wherein, the heat treatment may be conducted by heating means such as a hot plate, a hot air circulating furnace, an infrared heater, and the like, and it may be preferably conducted at 150 to 300° C., or 200 to 250° C.

Meanwhile, after the step of drying the coating (step 2), if necessary, a step of heat treating the dried coating to a temperature above the drying step may be further included. The heat treatment may be conducted by a hot plate, a hot air circulating furnace, an infrared heater, and the like, and preferably at 150° C. to 250° C. During this process, the liquid crystal alignment agent may be imidized.

Namely, the method for preparing a liquid crystal alignment film may comprise: applying the above explained liquid crystal alignment agent on a substrate to form a coating (step 1); drying the coating (step 2); heat treating the dried coating to a temperature above the drying step (step 3); irradiating light to the heat treated coating or rubbing the heat treated coating to progress alignment treatment (step 4); and heat treating the alignment-treated coating to cure (step 5).

4. Liquid Crystal Alignment Film

Meanwhile, according to yet another embodiment of the invention, a liquid crystal alignment film prepared according to the above explained method for preparing a liquid crystal alignment film is provided. Specifically, the liquid crystal alignment film may comprise the aligned and cured product of the liquid crystal alignment composition of one embodiment. The aligned and cured product means a product obtained through the alignment process and curing process of the liquid crystal alignment composition of one embodiment.

Specifically, the liquid crystal alignment film may have film strength calculated by the following Mathematical Formula 2, of 0.09% or less, 0.01% to 0.08%, 0.01% to 0.05%, or 0.02% to 0.04%.

Film strength=haze of liquid crystal alignment film after rubbing treatment−haze of liquid crystal alignment film before rubbing treatment    [Mathematical Formula 2]

The rubbing treatment of the liquid crystal alignment film may be conducted by rubbing the surface of the alignment film using rubbing machine of Sindo Enginnering while rotating at 850 rpm, and the haze value may be measured using a hazemeter.

Although the thickness of the liquid crystal alignment film is not specifically limited, for example, it may be controlled within 0.01 μM to 1000 μm. If the thickness of the liquid crystal alignment film increase or decreases by a specific numerical value, the properties measured in the liquid crystal alignment film may be also changed as much as the numerical value.

5. Liquid Crystal Display

And, according to yet another embodiment of the invention, a liquid crystal display comprising the above explained liquid crystal alignment film is provided The liquid crystal alignment film may be introduced in a liquid crystal cell by known methods, and the liquid crystal cell may be also introduced in the liquid crystal display by known methods. The liquid crystal alignment film is prepared from polymer comprising a specific content of repeat units represented by the Chemical Formula 1, and thus, excellent properties and excellent stability may be realized. Thus, a liquid crystal display capable of exhibiting high reliability is provided.

Meanwhile, the liquid crystal alignment display may have a voltage holding ratio (VHR) measured at 1 Hz, 60° C. using 6254C device of TOYO corporation, of 70% or more.

Advantageous Effects

According to the present invention, a cross-linking agent compound having excellent solubility and improved cross-linking effect; a liquid crystal alignment composition that may have improved dispersibility and thus high reliability, and may afford excellent film strength when synthesizing a liquid crystal alignment film, and simultaneously, may realize improved alignment property and electrical properties; a method for preparing a liquid crystal alignment film wherein the liquid crystal alignment composition is applied on a substrate and dried, and light is immediately irradiated to progress alignment treatment without high temperature heat treatment, and then, the alignment-treated coating is heat treated and cured, whereby light irradiation energy can be reduced, and a liquid crystal alignment film that has excellent alignment property and stability, has high voltage holding ratio even at high temperature, improves contrast ratio decrease or afterimage, and thus, has excellent electrical properties, can be provided by a simple process; and a liquid crystal alignment film and a liquid crystal display using the same, are provided.

DETAILED DESCRIPTION OF THE EMBODIMENTS

The present invention will be explained in more detail in the following examples. However, these examples are presented only as the illustrations of the present invention, and the contents of the present invention are not limited thereby.

Synthesis Example and Comparative Synthesis Example

Synthesis Example 1: Synthesis of a Cross-Linking Agent A1

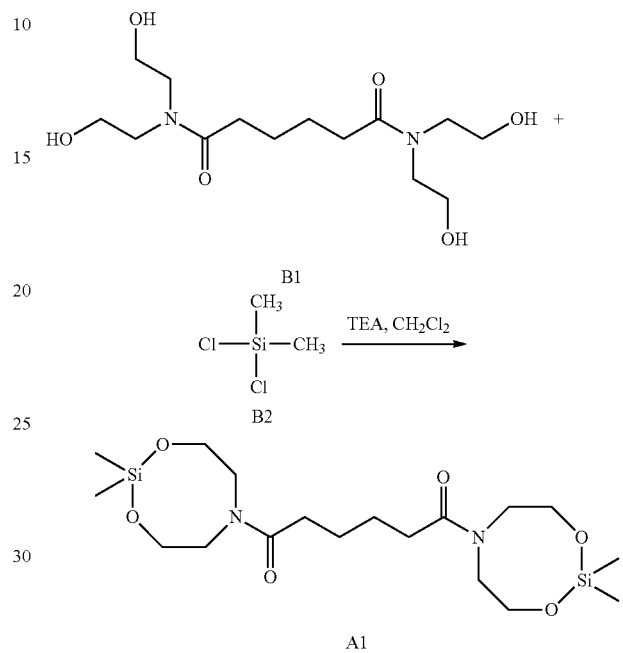

Under a nitrogen atmosphere, the compound B1 (10.0 g, 31.3 mmol) and triethylamine (19.0 g, 187.8 mmol) were dispersed in dichloromethane (200 mL), and then, a compound B2 (8.0 g, 62.6 mmol) was introduced, and the mixture was stirred at 0° C. for 2 hours, and at room temperature for 16 hours. After the reaction was completed, a saturated aqueous solution (300 ml) of sodium hydrogen carbonate was added, and the aqueous solution layer was extracted with dichloromethane (200 mL) twice. It was treated with magnesium sulfate (10 g) to dry. The filtrate was concentrated to prepare the cross-linking agent A1 (11.2 g, yield 82.5%)

MS [M+H]$^+$=433

Synthesis Example 2: Synthesis of a Cross-Linking Agent A2

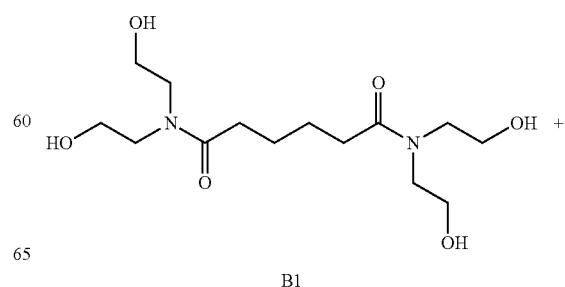

-continued

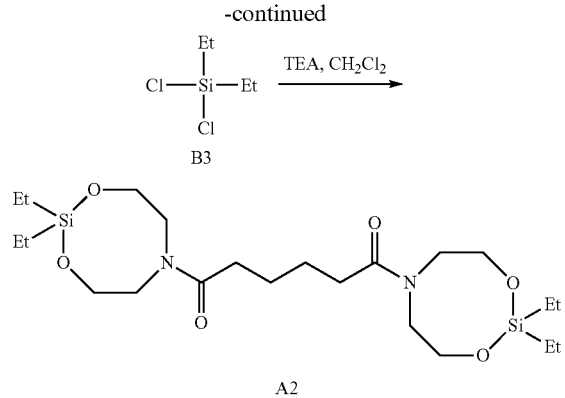

The cross-linking agent A2 was prepared by the same method as Synthesis Example 1, except that a compound B3 was used instead of the compound B2.

MS [M+H]$^+$=489

Synthesis Example 3: Synthesis of a Cross-Linking Agent A3

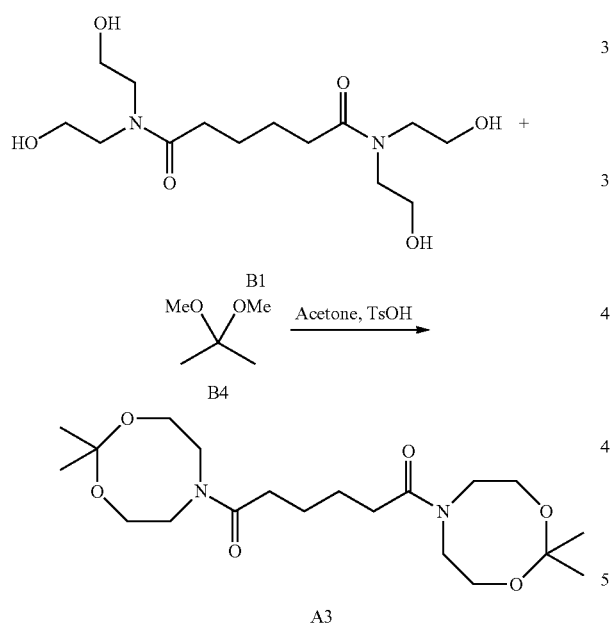

Under a nitrogen atmosphere, the compound B1 (10.0 g, 31.3 mmol) and the compound B4 (2,2-dimethoxypropane, 32.5 g, 313 mmol) were dissolved in anhydrous acetone (150 mL), and toluenesulfonic acid (0.52 g, 3.1 mmol) was introduced, and the mixture was stirred at room temperature for 12 hours. After the reaction was completed, a saturated aqueous solution (300 ml) of sodium hydrogen carbonate was added, and the aqueous solution layer was extracted with dichloromethane (200 mL) three times. It was treated with magnesium sulfate (10 g) to dry. The filtrate was concentrated to prepare the cross-linking agent A3 (9.3 g, yield 75.1%).

MS [M+H]$^+$=401

Synthesis Example 4: Synthesis of a Cross-Linking Agent A4

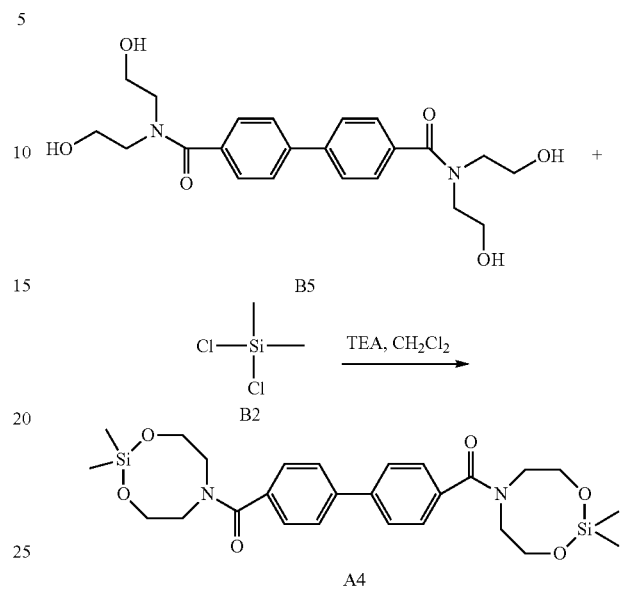

The cross-linking agent A4 was prepared by the same method as Synthesis Example 1, except that a compound B5 was used instead of the compound B1.

MS [M+H]$^+$=529

Synthesis Example 5: Synthesis of a Cross-Linking Agent A5

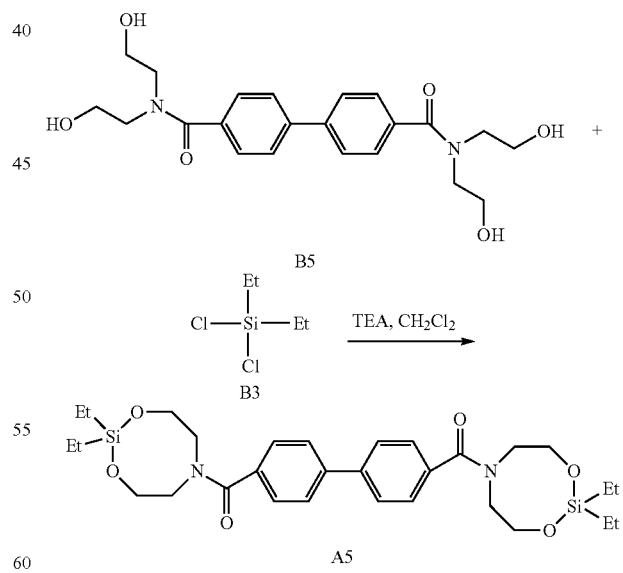

The cross-linking agent A5 was prepared by the same method as Synthesis Example 1, except that a compound B5 was used instead of the compound B1, and a compound B3 was used instead of the compound B2.

MS [M+H]$^+$=585

Synthesis Example 6: Synthesis of a Cross-Linking Agent A6

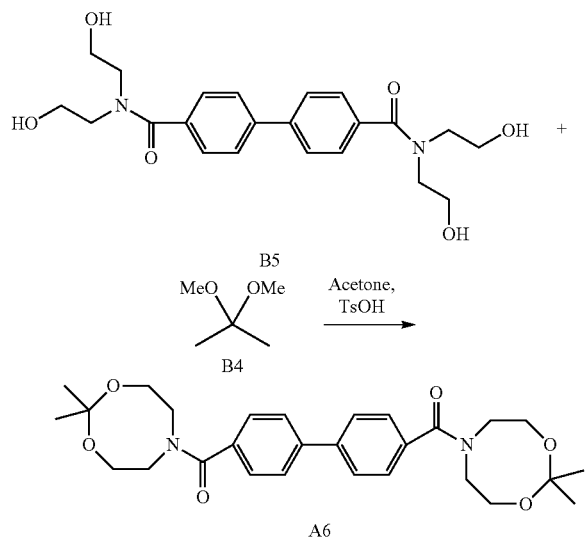

The cross-linking agent A6 was prepared by the same method as Synthesis Example 3, except that a compound B5 was used instead of the compound B1.

MS [M+H]$^+$=497

Synthesis Example 7: Synthesis of a Cross-Linking Agent A7

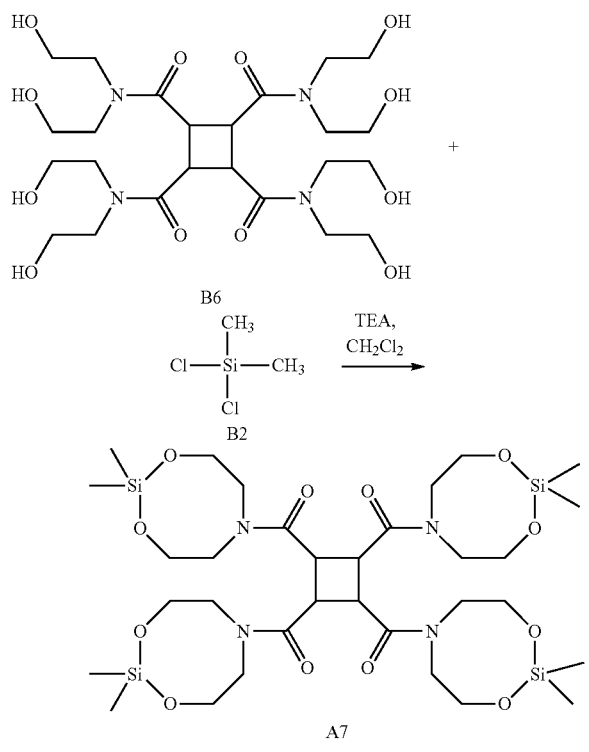

The cross-linking agent A7 was prepared by the same method as Synthesis Example 1, except that a compound B6 was used instead of the compound B1.

MS [M+H]$^+$=805

Synthesis Example 8: Synthesis of a Cross-Linking Agent A8

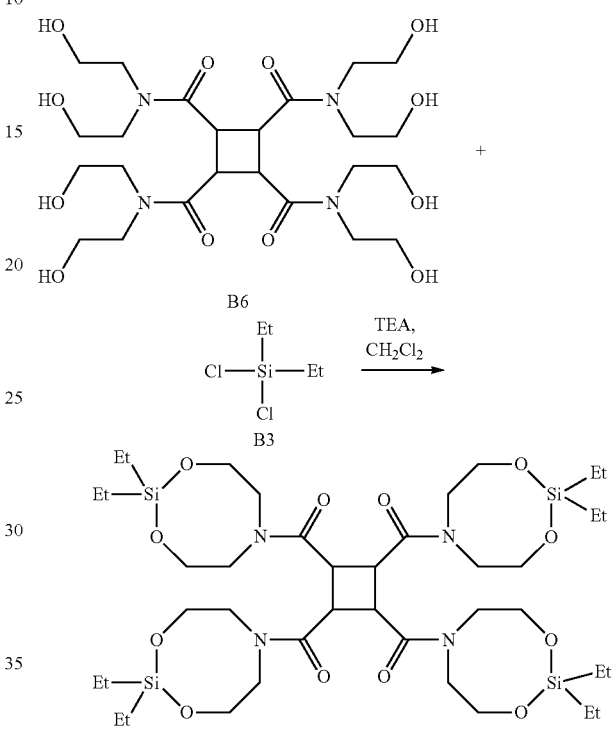

The cross-linking agent A8 was prepared by the same method as Synthesis Example 1, except that a compound B6 was used instead of the compound B1, and a compound B3 was used instead of the compound B2.

MS [M+H]$^+$=917

Synthesis Example 9: Synthesis of a Cross-Linking Agent A9

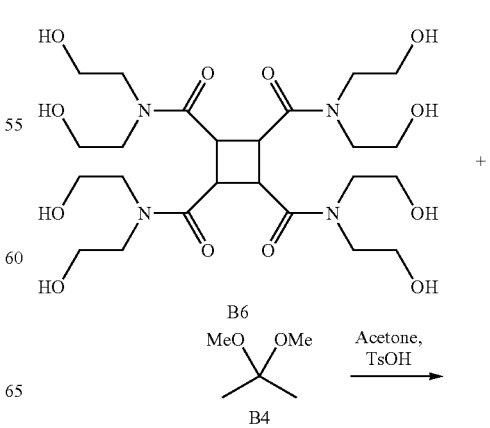

-continued

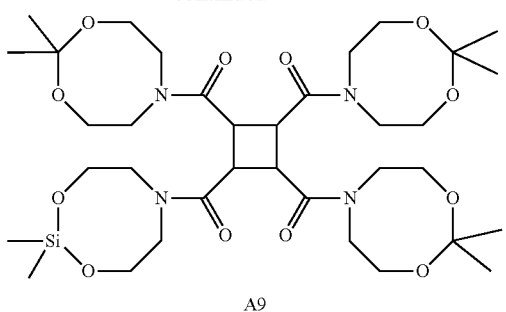

A9

The cross-linking agent A9 was prepared by the same method as Synthesis Example 3, except that a compound B6 was used instead of the compound B1.

MS [M+H]$^+$=741

Synthesis Example 10: Synthesis of a Cross-Linking Agent A10

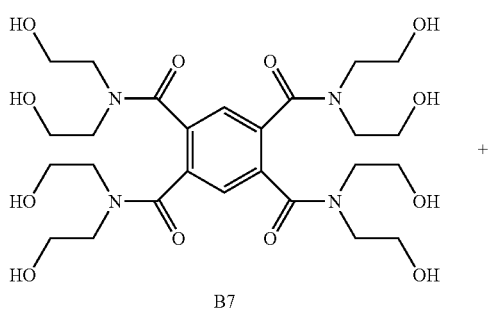

B7

+

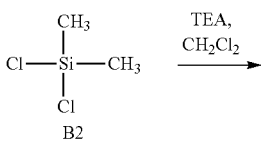

B2

A10

The cross-linking agent A10 was prepared by the same method as Synthesis Example 1, except that a compound B7 was used instead of the compound B1.

MS[M+H]$^+$=827

Synthesis Example 11: Synthesis of a Cross-Linking Agent A11

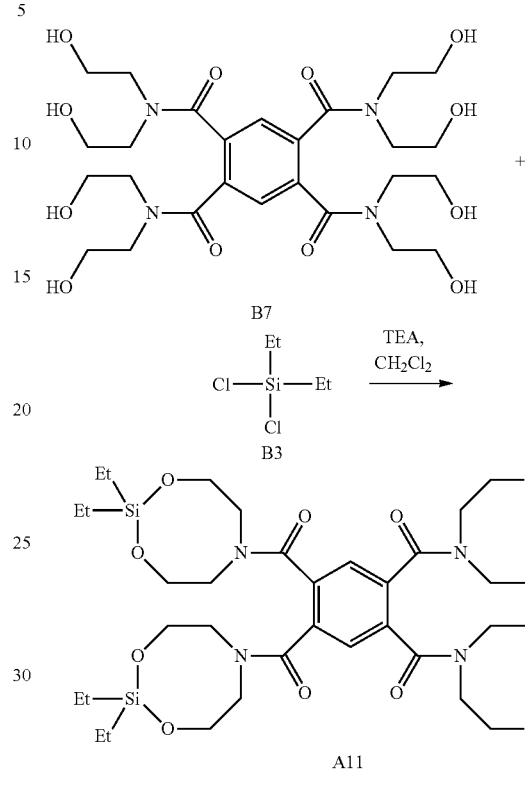

A11

The cross-linking agent A11 was prepared by the same method as Synthesis Example 1, except that a compound B7 was used instead of the compound B1, and a compound B3 was used instead of the compound B2.

MS [M+H]$^+$=939

Synthesis Example 12: Synthesis of a Cross-Linking Agent A12

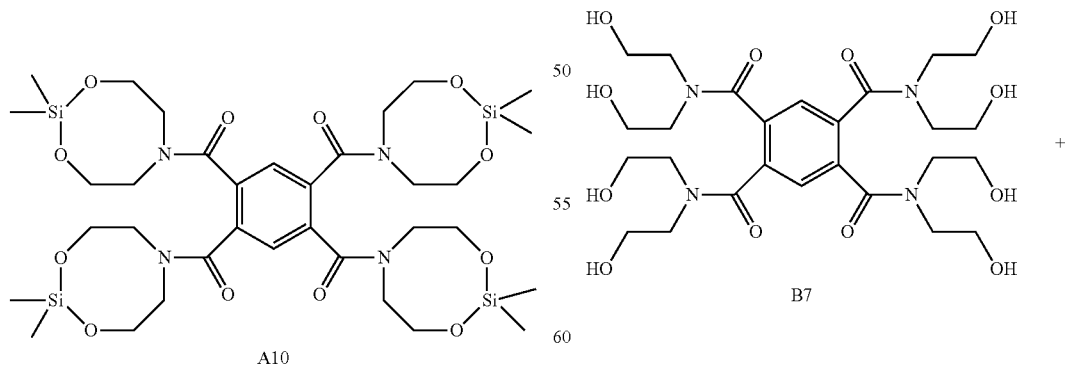

B7

+

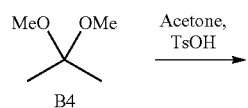

B4

-continued

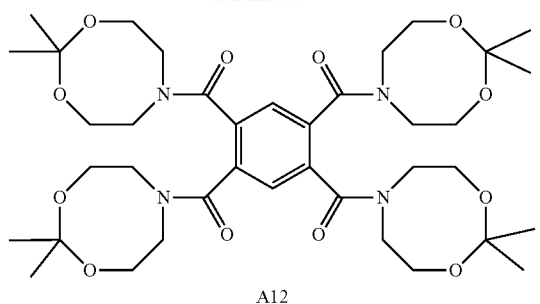

A12

The cross-linking agent A12 was prepared by the same method as Synthesis Example 3, except that a compound B7 was used instead of the compound B1.

MS [M+1-1]⁺=763

Synthesis Example 13: Synthesis of a Cross-Linking Agent A13

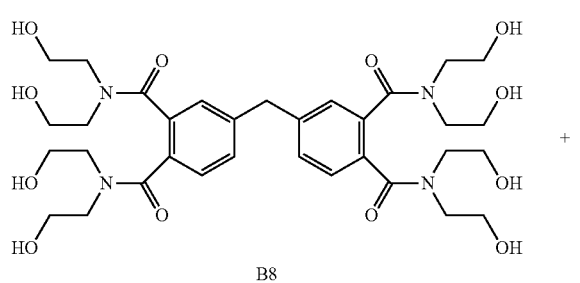

B8

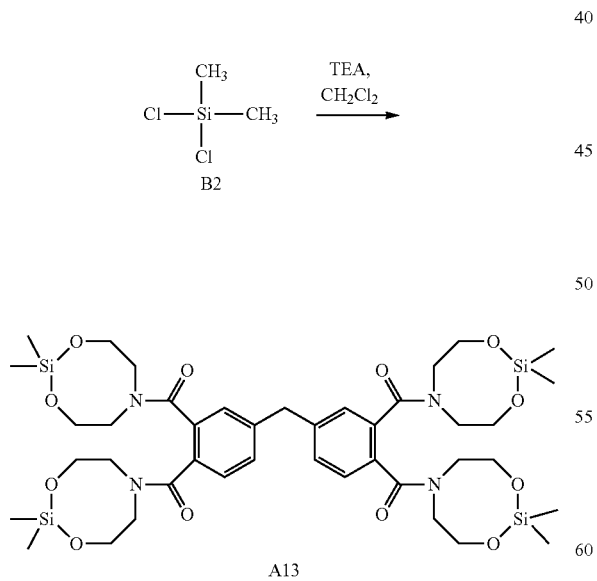

A13

The cross-linking agent A13 was prepared by the same method as Synthesis Example 1, except that a compound B8 was used instead of the compound B1.

MS[M+H]⁺=917

Synthesis Example 14: Synthesis of a Cross-Linking Agent A14

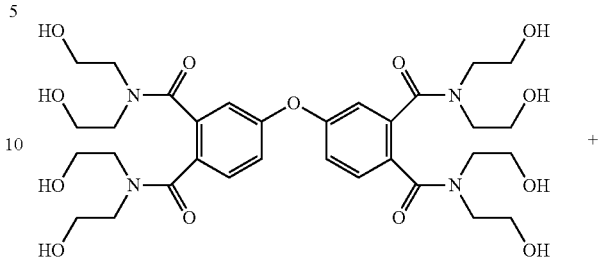

B9

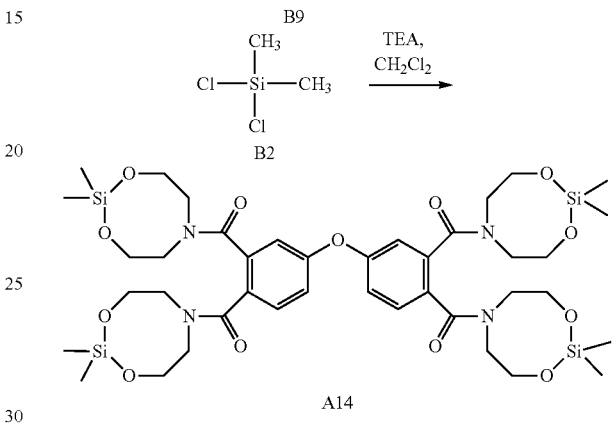

A14

The cross-linking agent A14 was prepared by the same method as Synthesis Example 1, except that a compound B9 was used instead of the compound B1.

MS[M+H]⁺=919

Synthesis Example 15: Synthesis of a Cross-Linking Agent A15

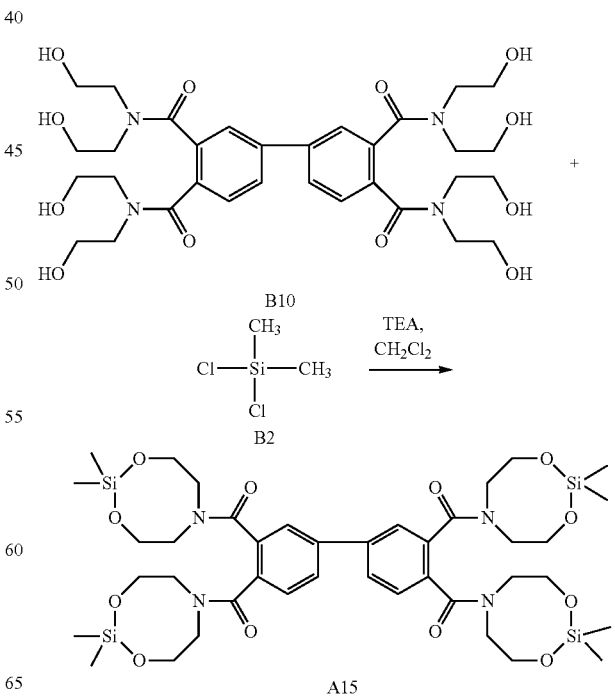

The cross-linking agent A15 was prepared by the same method as Synthesis Example 1, except that a compound B10 was used instead of the compound B1.

MS[M+H]$^+$=903

Synthesis Example 16: Synthesis of a Cross-Linking Agent A16

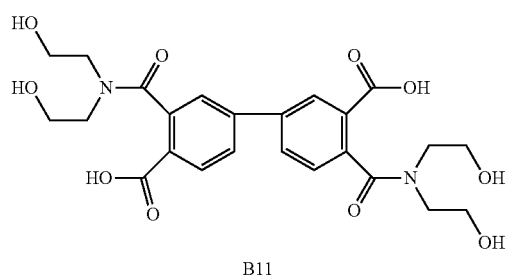

B11

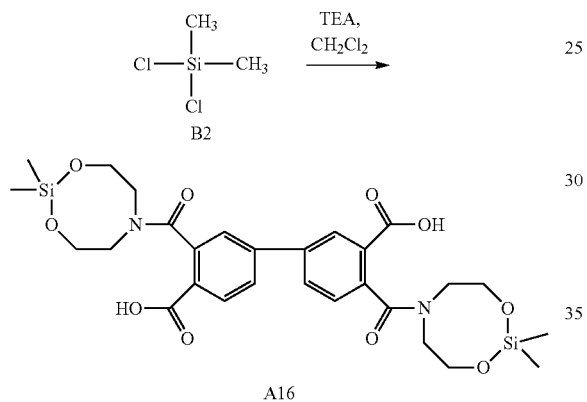

A16

The cross-linking agent A16 was prepared by the same method as Synthesis Example 1, except that a compound B11 was used instead of the compound B1.

MS [M+H]$^+$=617

Synthesis Example 17: Synthesis of a Cross-Linking Agent A17

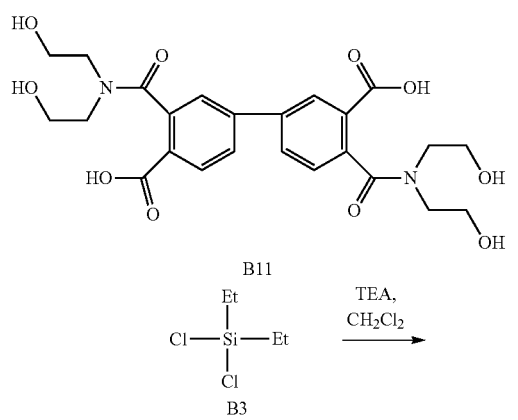

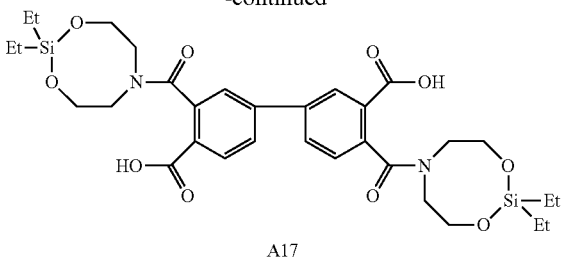

A17

The cross-linking agent A17 was prepared by the same method as Synthesis Example 1, except that a compound B11 was used instead of the compound B1, and a compound B3 was used instead of the compound B2.

MS [M+H]$^+$=673

Synthesis Example 18: Synthesis of a Cross-Linking Agent A18

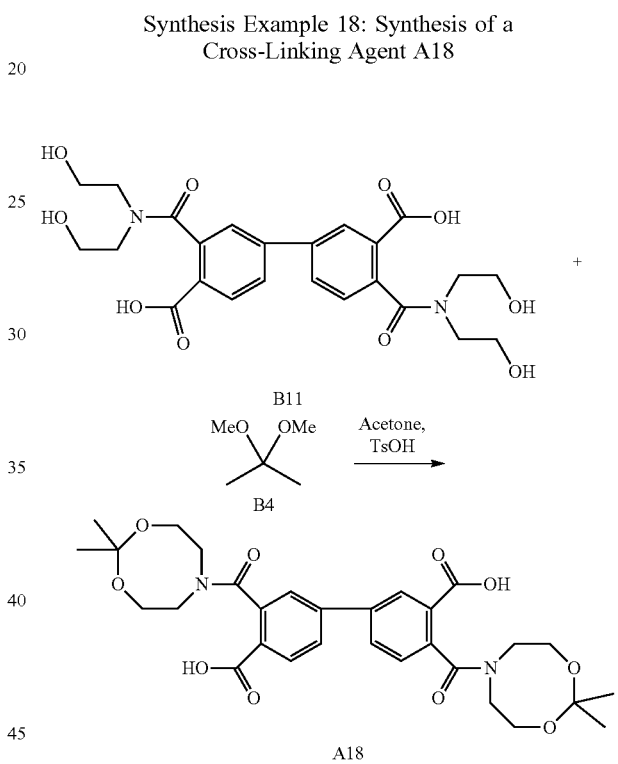

A18

The cross-linking agent A18 was prepared by the same method as Synthesis Example 3, except that a compound B11 was used instead of the compound B1.

MS [M+H]$^+$=585

Comparative Synthesis Example 1

The reactant of Synthesis Example 1, N,N,N',N'-Tetrakis (2-hydroxyethyl)adipamide was used as a cross-linking agent of Comparative Synthesis Example 1.

Example: Preparation of Liquid Crystal Alignment Compositions and Liquid Crystal Alignment Films Example Example 1: Preparation of a Liquid Crystal Alignment Composition 5.0 g (13.3 mmol) of diamine represented by the following Chemical Formula A, DA1 was completely dissolved in 71.27 g of anhydrous N-methyl pyrrolidone (NMP). And, under an ice bath, 2.92 g (13.03 mmol) of 1,3-dimethyl-cyclobutane-1,2,3,4-tetracarboxylic dianhydride (DMCBDA) was added to the solution, and the mixture was stirred at room temperature for about 16 hours to prepare liquid crystal alignment polymer P-1. As the result of confirming the molecular weight of the polymer P-1 by GPC, the number average molecular weight (Mn) was 15500 g/mol, and the weight average molecular weight (Mw) was 31000 g/mol And, the monomer structure of the polymer P-1 is determined by the equivalent ratio of monomers used, wherein the rate of imide structures in the molecule was 50.5%, and the rate of amic acid structures was 49.5%.

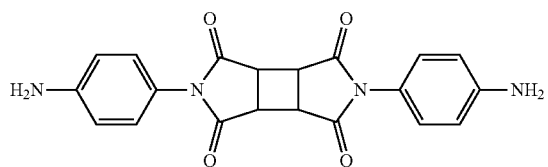 [SMILES: Nc1ccc(N2C(=O)C3C(C2=O)C2C(=O)N(c4ccc(N)cc4)C(=O)C32)cc1]

19.743 g (0.099 mol) of diamine represented by the following Chemical Formula B, DA2 was completely dissolved in 225.213 g of anhydrous N-methylpyrrolidone (anhydrous N-methyl pyrrolidone: NMP). And, under an ice bath, 20.0 g (0.092 mol) of pyromellitic dianhydride (PMDA) was added to the solution, and the mixture was stirred at room temperature for about 16 hours to prepare liquid crystal alignment polymer Q-1. As the result of confirming the molecular weight of the polymer Q-1 by GPC, the weight average molecular weight (Mw) was 27000 g/mol.

[Chemical Formula B]

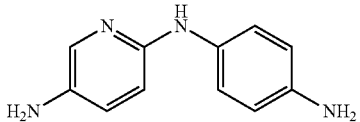

10 g of the liquid crystal alignment polymer P-1 and 10 g of the liquid crystal alignment polymer Q-1 were put in 12.4 g of NMP and 7.6 g of n-buthoxyethanol (weight ratio 8:2) to obtain a 5 wt % solution. And, to the solution, the cross-linking agent A1 obtained in Synthesis Example 1 was added as a cross-linking agent in the content of 3 wt % based on the total solution, and then, the solution was stirred at 25° C. for 16 hours. The obtained solution was filtered under pressure with a filter made of poly(tetrafluoroethylene), having a pore size of 0.1 fall, thus preparing a liquid crystal alignment composition.

Examples 2 to 18: Preparation of Liquid Crystal Alignment Compositions

Liquid crystal alignment compositions were prepared by the same method as Example 1, except that the cross-linking agent A2 to cross-linking agent A18 obtained in Synthesis Example 2 to 18 were used instead of the cross-linking agent A1 obtained in Synthesis Example 1, with the composition described in the following Table 1.

Comparative Example 1: Preparation of a Liquid Crystal Alignment Composition A liquid crystal alignment composition was prepared by the same method as Example 1, except that the cross-linking agent A1 obtained in Synthesis Example 1 was not added.

Comparative Example 2: Preparation of a Liquid Crystal Alignment Composition A liquid crystal alignment composition was prepared by the same method as Example 1, except that N,N,N',N'-Tetrakis(2-hydroxyethyl)adipamide of Comparative Synthesis Example 1 was added instead of the cross-linking agent A1 obtained in Synthesis Example 1.

The compositions of the liquid crystal alignment compositions of Examples and Comparative Examples are summarized in the following Table 1.

TABLE 1

| | First polymer | | Second polymer | | Mixing ratio of first and second polymer | cross-linking agent | |
|---|---|---|---|---|---|---|---|
| | kind | input (g) | kind | Input (g) | | kind | input (wt %) |
| Example 1 | P-1 | 10 | Q-1 | 10 | 50:50 | cross-linking agent A1 | 3 |
| Example 2 | P-1 | 10 | Q-1 | 10 | 50:50 | cross-linking agent A2 | 3 |
| Example 3 | P-1 | 10 | Q-1 | 10 | 50:50 | cross-linking agent A3 | 3 |
| Example 4 | P-1 | 10 | Q-1 | 10 | 50:50 | cross-linking agent A4 | 3 |
| Example 5 | P-1 | 10 | Q-1 | 10 | 50:50 | cross-linking agent A5 | 3 |
| Example 6 | P-1 | 10 | Q-1 | 10 | 50:50 | cross-linking agent A6 | 3 |
| Example 7 | P-1 | 10 | Q-1 | 10 | 50:50 | cross-linking agent A7 | 3 |
| Example 8 | P-1 | 10 | Q-1 | 10 | 50:50 | cross-linking agent A8 | 3 |
| Example 9 | P-1 | 10 | Q-1 | 10 | 50:50 | cross-linking agent A9 | 3 |
| Example 10 | P-1 | 10 | Q-1 | 10 | 50:50 | cross-linking agent A10 | 3 |
| Example 11 | P-1 | 10 | Q-1 | 10 | 50:50 | cross-linking agent A11 | 3 |
| Example 12 | P-1 | 10 | Q-1 | 10 | 50:50 | cross-linking agent A12 | 3 |
| Example 13 | P-1 | 10 | Q-1 | 10 | 50:50 | cross-linking agent A13 | 3 |
| Example 14 | P-1 | 10 | Q-1 | 10 | 50:50 | cross-linking agent A14 | 3 |
| Example 15 | P-1 | 10 | Q-1 | 10 | 50:50 | cross-linking agent A15 | 3 |
| Example 16 | P-1 | 10 | Q-1 | 10 | 50:50 | cross-linking agent A16 | 3 |

TABLE 1-continued

|  | First polymer | | Second polymer | | Mixing ratio of first and second polymer | cross-linking agent | |
| --- | --- | --- | --- | --- | --- | --- | --- |
|  | kind | input (g) | kind | Input (g) |  | kind | input (wt %) |
| Example 17 | P-1 | 10 | Q-1 | 10 | 50:50 | cross-linking agent A17 | 3 |
| Example 18 | P-1 | 10 | Q-1 | 10 | 50:50 | cross-linking agent A18 | 3 |
| Comparative Example 1 | P-1 | 10 | Q-1 | 10 | 50:50 | — | — |
| Comparative Example 2 | P-1 | 10 | Q-1 | 10 | 50:50 | Comparative 3 Synthesis Example1 |  |

Experimental Example

Preparation of a Liquid Crystal Alignment Cell

A liquid crystal alignment film and a liquid crystal alignment cell were prepared using each liquid crystal alignment composition prepared in Examples and Comparative Examples.

Specifically, on the upper and lower substrates for voltage holding ratio (VHR) in which an ITO electrode of 1 cm×1 cm, 60 nm thickness was patterned on a 2.5 cm×2.7 cm rectangular glass substrate, a liquid crystal alignment composition was respectively applied by spin coating. Subsequently, the substrates coated with the liquid crystal alignment agent were placed on a hot plate of about 70° C., and dried for 3 minutes to evaporate solvents. In order to progress alignment treatment of the obtained coating, each coating of the upper/lower substrates was irradiated by 254 nm UV rays at the exposure of 0.1-1.0 Poi using an exposure equipment to which a line polarizer is attached. Thereafter, the alignment-treated upper/lower substrates were baked (cured) in an oven of about 230° C. to obtain liquid crystal alignment films respectively having a film thickness of 0.1 μm.

Thereafter, a sealing agent into which a 4.5 fall ball spacer was impregnated was applied at the edge of the upper substrate except a liquid crystal inlet. And, the upper and lower substrates were arranged such that the liquid crystal alignment films formed thereon face each other and the alignment directions are parallel to each other, and then, the upper and lower substrates were combined, and by UV and thermal curing of the sealing agent, an empty cell was prepared. And, into the empty cell, liquid crystal was introduced, and the inlet was sealed with a sealing agent, thus preparing a liquid crystal alignment cell.

1) Evaluation of Liquid Crystal Alignment Property

To the upper and lower substrates of the liquid crystal cell prepared above, polarization plates were attached perpendicularly to each other. Wherein, the polarization axis of the polarization plate attached to the lower substrate was made parallel to the alignment axis of the liquid crystal cell. And, the liquid crystal cell to which the polarization plates were attached was placed on a backlight with a brightness of 7,000 cd/m², and light leak was observed with the unaided eye. Wherein, if the alignment property of the liquid crystal alignment film is excellent and liquid crystal is arranged well, light may not pass through the upper and lower polarization plates attached perpendicularly to each other, and it may be observed dark without defects. Such a case was indicated as 'good', and if light leak such as bright point or liquid crystal flow mark is observed, indicated as 'bad' in the Table 2.

2) Evaluation of Liquid Crystal Alignment Stability

To the upper and lower substrates of the liquid crystal alignment cell prepared above, polarization plates were attached perpendicularly to each other. The liquid crystal cell to which the polarization plates were attached was placed on a backlight of 7,000 cd/m², and luminance in the state of black was observed using a luminance meter PR-788 of PHOTO RESEARCH Company. And, the liquid crystal was driven at room temperature, alternating current voltage of 5V for 24 hours. Thereafter, while the voltage of the liquid crystal cell was turned off, luminance in the state of black was observed as explained above. A difference between the initial luminance (L0) measured before driving the liquid crystal cell and the later luminance (L1) measured after driving was divided by the initial luminance (L0) and multiplied by 100, thus calculating luminance change rate. As the calculated luminance change rate is closer to 0%, it means that alignment stability is excellent. Through the measurement result of luminance change rate, the level of afterimage was evaluated according to the following standard. It is preferable that AC afterimage is minimized, and in the measurement result, if the luminance change rate is less than 10%, it is evaluated as 'excellent'; if the luminance change rate is 10% to 20%, evaluated as 'average'; and if the luminance change rate is greater than 20%, evaluated as 'bad', and the results were shown in the following Table 2.

3) Measurement of Voltage Holding Ratio (VHR)

The electrical property, voltage holing ratio (VHR) of the obtained liquid crystal alignment cell was measured using 6254 equipment of Toyo Company. The voltage holding ratio was measured under severe condition of 1 V, 1 Hz, 60° C. The voltage holding ratio of 100% is ideal, and if the measurement result is 70% or more, evaluated as 'good', and if it is less than 70%, evaluated as 'bad', and the results were shown in the following Table 2.

4) Solubility

To each cross-linking agent used in the liquid crystal alignment compositions of Examples and Comparative Examples, a solvent (y-butyrolactone) was added such that the added amount of cross-linking agents described in Table 1 may be fulfilled, and then, the mixture was stirred for 10 seconds to prepare a mixed solution, the transparency of the mixed solution was confirmed with the unaided eye, and the solubility was evaluated according to the following standard.

In the measurement result, if the mixed solution is transparent, evaluated as 'excellent', if it is opaque, evaluated as 'bad', and the results were shown in the following Table 2.

5) Film Strength

For the above obtained liquid crystal alignment films, the surface of each liquid crystal alignment film was rubbed while rotating at 850 rpm using rubbing machine of Sindo Engineering, and then, a haze value was measured using a hazemeter, and a difference with a haze value before rubbing was calculated by the following Mathematical Formula 2, thus evaluating film strength. If the haze change is less than 1, film strength is excellent.

Film strength=haze of liquid crystal alignment film after rubbing−haze of liquid crystal alignment film before rubbing      [Mathematical Formula 2]

TABLE 2

| | Evaluation of liquid crystal alignment property | Evaluation of liquid crystal alignment stability | Evaluation of voltage holding ratio | Film strength (%) | solubility |
|---|---|---|---|---|---|
| Example 1 | Good | Excellent | Good | 0.04 | Excellent |
| Example 2 | Good | Excellent | Good | 0.03 | Excellent |
| Example 3 | Good | Excellent | Good | 0.04 | Excellent |
| Example 4 | Good | Excellent | Good | 0.04 | Excellent |
| Example 5 | Good | Excellent | Good | 0.03 | Excellent |
| Example 6 | Good | Excellent | Good | 0.04 | Excellent |
| Example 7 | Good | Excellent | Good | 0.03 | Excellent |
| Example 8 | Good | Excellent | Good | 0.02 | Excellent |
| Example 9 | Good | Excellent | Good | 0.03 | Excellent |
| Example 10 | Good | Excellent | Good | 0.04 | Excellent |
| Example 11 | Good | Excellent | Good | 0.03 | Excellent |
| Example 12 | Good | Excellent | Good | 0.03 | Excellent |
| Example 13 | Good | Excellent | Good | 0.03 | Excellent |
| Example 14 | Good | Excellent | Good | 0.03 | Excellent |
| Example 15 | Good | Excellent | Good | 0.04 | Excellent |
| Example 16 | Good | Excellent | Good | 0.03 | Excellent |
| Example 17 | Good | Excellent | Good | 0.04 | Excellent |
| Example 18 | Good | Excellent | Good | 0.04 | Excellent |
| Comparative Example 1 | Good | Excellent | Bad | 1.71 | Bad |
| Comparative Example 2 | Good | Excellent | Good | 0.09 | Bad |

As shown in Table 2, the liquid crystal alignment compositions of Examples containing the cross-linking agents of Synthesis Examples 1 to 18 had very low haze change values before and after rubbing (0.02% to 0.04%), thus confirming excellent film strength.

It seems to result from the cross-linking agents of Synthesis Examples 1 to 18 used in the liquid crystal alignment compositions of Examples. Specifically, in order to evaluate the solubilities of the cross-linking agents of Synthesis Examples 1 to 18 in y-butyrolactone solvent, the transparencies of each solution before/after adding the cross-linking agent were confirmed with the unaided eye. As the result, the liquid crystal alignment compositions of Examples containing the cross-linking agents of Synthesis Examples 1 to 18 were observed transparent, and thus, it can be seen that they have excellent solubilities.

Thus, it was confirmed that since the cross-linking agents of Synthesis Examples 1 to 18 have very excellent solubility in the solvent commonly used in a liquid crystal alignment composition, even if the cross-linking agents are added in a relatively small amount, performance of the liquid crystal alignment film can be improved with high efficiency, and dispersibility in the liquid crystal alignment composition can be increased, thereby increasing reliability of the finally prepared liquid crystal alignment film.

To the contrary, in the case of the alignment film obtained from the liquid crystal alignment composition of Comparative Example 1 that does not contain any cross-linking agents of Synthesis Example 1 to 18, a haze change value before and after rubbing rapidly increases to 1.71%, thus confirming very bad film strength.

Meanwhile, in the case of the cross-linking agent of Comparative Synthesis Example 1 used in the liquid crystal alignment agent of Comparative Example 2, as the result of confirming the transparencies of the solution before/after adding the cross-linking agent, it was observed as opaque suspension, thus confirming that the solubility in the solvent rapidly decreased compared to the Examples of the present invention. Thus, it was confirmed that the cross-linking agent of Comparative Synthesis Example 1 has very poor solubility in the solvent commonly used in a liquid crystal alignment composition, and thus, dispersibility in the liquid crystal alignment composition decreases, and reliability of the finally prepared liquid crystal alignment film decreases.

The invention claimed is:

1. A cross-linking agent compound represented by the following Chemical Formula 1:

[Chemical Formula 1]

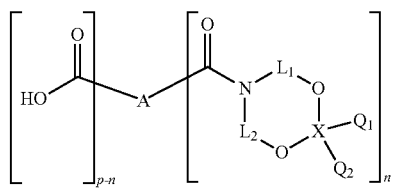

in the Chemical Formula 1,

A is a p-valent functional group, p is an integer of 1 to 4 provided that p is equal to or greater than n, n is an integer of 1 to 4, $L_1$ and $L_2$ are identical to or different from each other, and each independently, a C1-10 alkylene group, $Q_1$ and $Q_2$ are identical to or different from each other, and each independently, hydrogen, a C1-10 alkyl group, or a C6-20 aryl group, and X is a Group 14 element selected from carbon (C), silicon (Si), germanium (Ge), tin (Sn), and lead (Pb).

2. The cross-linking agent compound according to claim 1, wherein

A is a C1-10 alkylene group or a C6-30 arylene group, p is 2, and n is 2.

3. The cross-linking agent compound according to claim 1, wherein

A is one of tetravalent functional groups represented by the following Chemical Formula 2, p is 4, and n is 2 or 4:

[Chemical Formula 2]

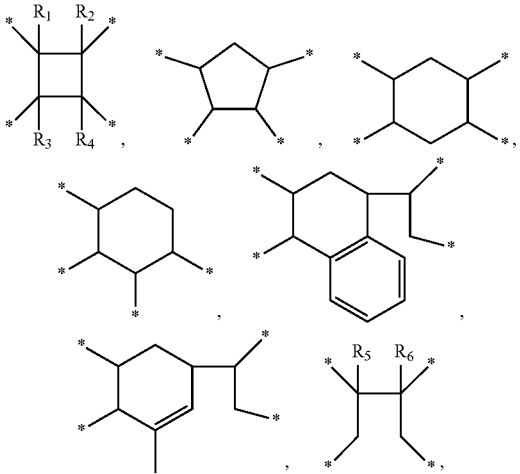

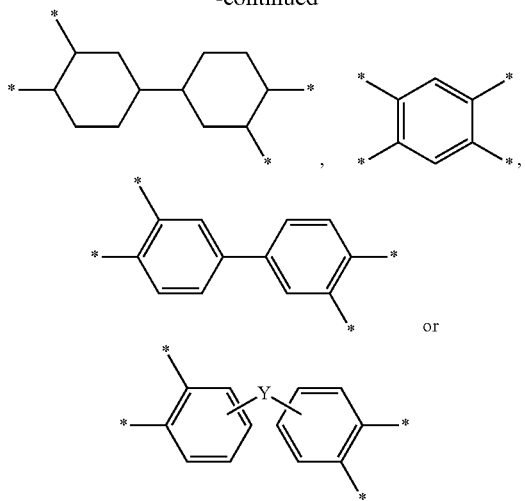

in the Chemical Formula 2, $R_1$ to $R_6$ are each independently, hydrogen, or a C1-10 alkyl group, Y is one selected from the group consisting of a direct bond, —O—, —CO—, —S—, —SO—, —SO$_2$—, —CR$_7$R$_8$—, —CONH—, —COO—, —(CH$_2$)$_b$—, —O(CH$_2$)$_b$O—, —COO—(CH$_2$)$_b$—OCO—, phenylene, or a combination thereof, $R_7$ and $R_8$ are each independently, hydrogen, a C1-10 alkyl group, or a C1-10 haloalkyl group, and b is an integer of 1 to 10.

4. The cross-linking agent compound according to claim 1, wherein $L_1$ and $L_2$ are identical to or different from each other, and each independently, a C1-5 alkylene group, and $Q_1$ and $Q_2$ identical to or different from each other, and each independently, a C1-10 alkyl group.

5. The cross-linking agent compound according to claim 1, wherein X is C or Si.

6. The cross-linking agent compound according to claim 1, wherein the cross-linking agent compound represented by the Chemical Formula 1 includes compounds represented by the following Chemical Formula 1-1 to Chemical Formula 1-3:

[Chemical Formula 1-1]

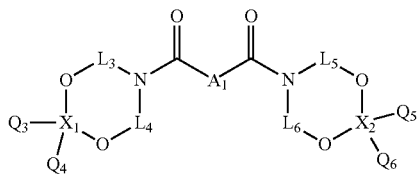

in the Chemical Formula 1-1, $A_1$ is a divalent functional group, $L_3$ to $L_6$ are identical to or different from each other, and each independently, a C1-10 alkylene group, $Q_3$ to $Q_6$ are identical to or different from each other, and each independently, a C1-10 alkyl group or a C6-20 aryl group, and $X_1$ and $X_2$ are each independently, a Group 14 element selected from carbon (C), silicon (Si), germanium (Ge), tin (Sn), and lead (Pb),

[Chemical Formula 1-2]

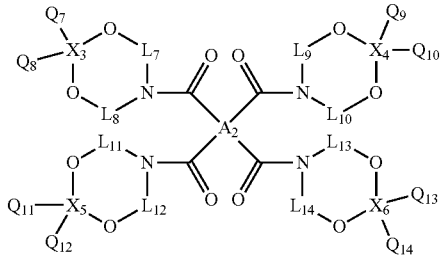

in the Chemical Formula 1-2, $A_2$ is a tetravalent functional group, $L_7$ to $L_{14}$ are identical to or different from each other, and each independently, a C1-10 alkylene group, $Q_7$ to $Q_{14}$ are identical to or different from each other, and each independently, a C1-10 alkyl group or a C6-20 aryl group, and $X_3$ to $X_6$ are each independently, a Group 14 element selected from carbon (C), silicon (Si), germanium (Ge), tin (Sn), and lead (Pb),

[Chemical Formula 1-3]

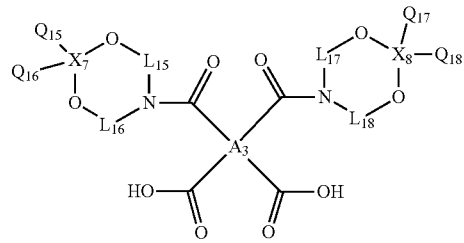

in the Chemical Formula 1-3, $A_3$ is a tetravalent functional group, $L_{15}$ to $L_{18}$ are identical to or different from each other, and each independently, a C1-10 alkylene group, $Q_{15}$ to $Q_{18}$ are identical to or different from each other, and each independently, a C1-10 alkyl group or a C6-20 aryl group, and $X_7$ to $X_8$ are each independently, a Group 14 element selected from carbon (C), silicon (Si), germanium (Ge), tin (Sn), and lead (Pb).

7. A liquid crystal alignment composition comprising
the cross-linking agent compound of claim 1; and
a liquid crystal alignment polymer comprising one or more repeat units selected from polyamic acid repeat units, polyamic acid ester repeat units, and polyimide repeat units.

8. The liquid crystal alignment composition according to claim 7, wherein the liquid crystal alignment polymer comprises
a first liquid crystal alignment polymer comprising one or more repeat units selected from repeat units represented by the following Chemical Formula 4, repeat units represented by the following Chemical Formula 5, and repeat units represented by the following Chemical Formula 6; and
a second liquid crystal alignment polymer comprising one or more repeat units selected from repeat units represented by the following Chemical Formula 7, repeat units represented by the following Chemical Formula 8, and repeat units represented by the following Chemical Formula 9:

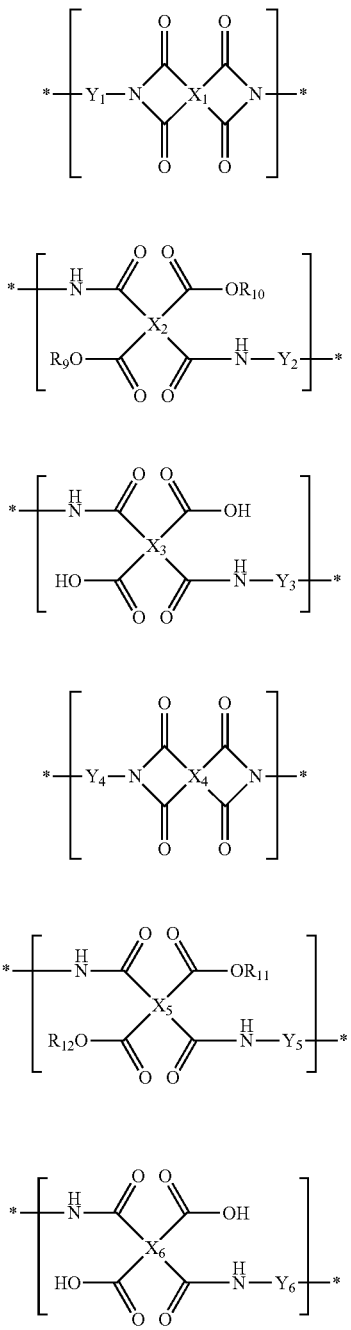

[Chemical Formula 4]

[Chemical Formula 5]

[Chemical Formula 6]

[Chemical Formula 7]

[Chemical Formula 8]

[Chemical Formula 9]

in the Chemical Formulaes 4 to 9, at least one of $R_9$ and $R_{10}$ is a C1-10 alkyl group, and the other is hydrogen, at least one of $R_{11}$ and $R_{12}$ is a C1-10 alkyl group, and the other is hydrogen, $X_1$ to $X_6$ are each independently, a tetravalent organic group represented by the following Chemical Formula 10,

[Chemical Formula 10]

in the Chemical Formula 10, $R_{13}$ to $R_{18}$ are each independently, hydrogen, or a C1-6 alkyl group, L' is one selected from a single bond, —O—, —CO—, —COO—, —S—, —SO—, —SO$_2$—, —CR$_{19}$R$_{20}$—, —(CH$_2$)$_Z$—, —O(CH$_2$)$_Z$O—, —COO(CH$_2$)$_Z$OCO—, —CONH—, and phenylene, wherein $R_{19}$ and $R_{20}$ are each independently, hydrogen, a C1-10 alkyl group, or a C1-10 haloakyl group, and z is an integer of 1 to 10, $Y_1$ to $Y_3$ are each independently, a divalent organic group represented by the following Chemical Formula 11,

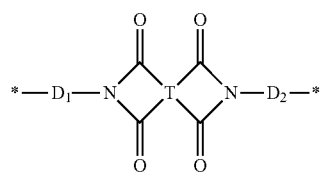

[Chemical Formula 11]

in the Chemical Formula 11,

T is a tetravalent organic group represented by the Chemical Formula 10, $D_1$ and $D_2$ are each independently, a C1-20 alkylene group, a C1-10 heteroalkylene group, a C3-20 cycloalkylene group, a C6-20 arylene group, or a C2-20 heteroarylene group, $Y_4$ to $Y_6$ are each independently, a divalent organic group represented by the following Chemical Formula 12,

[Chemical Formula 12]

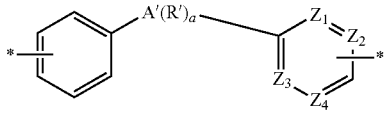

in the Chemical Formula 12,

A' is a Group 15 element selected from nitrogen (N), phosphorus (P), arsenic (As), antimony (Sb) and bismuth (Bi), R' is hydrogen, or a C1-10 alkyl group, a is an integer of 1 to 3, and at least one of $Z_1$ to $Z_4$ is nitrogen, and the others are carbon.

9. The liquid crystal alignment composition according to claim 7, comprising the cross-linking agent compound represented by the Chemical Formula 1 in an amount of 1 to 30 wt %, based on the total weight of the liquid crystal alignment composition.

10. A method for preparing a liquid crystal alignment film, comprising steps of:

applying the liquid crystal alignment composition of claim 8 on a substrate to form a coating;

drying the coating;

irradiating light to the coating or rubbing the coating to progress alignment treatment; and heat treating the alignment-treated coating to cure.

11. The method according to claim 10, wherein in the step of heat treating the alignment-treated coating to cure, a cross-linking agent compound represented by the following Chemical Formula 3 is included in the alignment-treated coating:

[Chemical Formula 3]

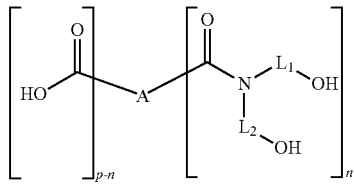

in the Chemical Formula 3,

A is a p-valent functional group, p is an integer of 1 to 4 provided that p is equal to or greater than n, n is an integer of 1 to 4, and $L_1$ and $L_2$ are identical to or different from each other, and each independently, a C1-10 alkylene group.

12. A liquid crystal alignment film comprising the aligned and cured product of the liquid crystal alignment composition of claim 7.

13. A liquid crystal display comprising the liquid crystal alignment film of claim 12.

* * * * *